United States Patent
Battaglia et al.

(10) Patent No.: US 8,562,974 B2
(45) Date of Patent: Oct. 22, 2013

(54) METHOD FOR EXPANDING CD4+ CD25+ T REGULATOR CELLS

(75) Inventors: Manuela Battaglia, Milan (IT); Maria Grazia Roncarolo, Milan (IT)

(73) Assignees: Fondazione Telethon, Rome (IT); Ospedale San Raffaele S.R.L., Milan (IT)

( * ) Notice: Subject to any disclaimer, the term of this patent is extended or adjusted under 35 U.S.C. 154(b) by 368 days.

(21) Appl. No.: 11/815,080

(22) PCT Filed: Feb. 26, 2006

(86) PCT No.: PCT/IB2006/001116
§ 371 (c)(1),
(2), (4) Date: Jul. 14, 2008

(87) PCT Pub. No.: WO2006/090291
PCT Pub. Date: Aug. 31, 2006

(65) Prior Publication Data
US 2008/0279826 A1 Nov. 13, 2008

(30) Foreign Application Priority Data
Feb. 25, 2005 (GB) .................................. 0503936.7

(51) Int. Cl.
*A01N 63/00* (2006.01)
*C12N 5/071* (2010.01)

(52) U.S. Cl.
USPC ..................................... 424/93.71; 435/372.3

(58) Field of Classification Search
None
See application file for complete search history.

(56) References Cited

U.S. PATENT DOCUMENTS

| | | |
|---|---|---|
| 3,929,992 A | 12/1975 | Sehgal et al. |
| 4,316,885 A | 2/1982 | Rakhit et al. |
| 4,650,803 A | 3/1987 | Stella et al. |
| 5,023,263 A | 6/1991 | Von Burg |
| 5,023,264 A | 6/1991 | Caufield et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,151,413 A | 9/1992 | Caufield et al. |
| 5,162,333 A | 11/1992 | Failli et al. |
| 5,177,203 A | 1/1993 | Failli et al. |
| 5,221,670 A | 6/1993 | Caufield |
| 5,233,036 A | 8/1993 | Hughes |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,302,584 A | 4/1994 | Kao et al. |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,463,048 A | 10/1995 | Skotnicki et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,563,145 A | 10/1996 | Failli et al. |
| 5,665,772 A | 9/1997 | Cottens et al. |
| 5,780,462 A | 7/1998 | Lee et al. |
| 2003/0147865 A1* | 8/2003 | Salomon et al. ........... 424/93.21 |
| 2005/0031611 A1 | 2/2005 | Strom et al. |

FOREIGN PATENT DOCUMENTS

| | | |
|---|---|---|
| WO | WO 01/97809 | 12/2001 |
| WO | WO 2004/050090 | 6/2004 |
| WO | WO 2005003335 A2 * | 1/2005 |
| WO | WO 2005010215 A2 * | 2/2005 |

OTHER PUBLICATIONS

Henderson et al., 1991, Immuno.. vol. 73: 316-321.*
Arceci et al., 1992, Blood. vol. 80: 1528-1536.*
Zheng et al., 2003, Immunity. vol. 19: 503-541.*
National Cancer Institute Defintion for Everolimus,2011, p. 1.*
Homann et al., 2005, pp. 19-38.*
Li et al., 2008, J. Virol. vol. 82: 21-30.*
Delgoffe et al., 2009, Immunology, vol. 127: 459-465.*
Wang et al., 2011, British J. cancer, vol. 104: 643-652.*
Game et al., Published online Feb. 11, 2005, Am J. Transp. vol. 5: 454-464.*
MS the Disease, National Multiple Sclerosis Society, 2012, pp. 1-4.*
Golovina et al., 2008, J. Immunol. vol. 181: 2855-2868.*
Hoffmann et al., 2004, Blood. vol. 104: 895-903.*
Keever-Taylor et al., 2007: Cytotherapy vol. 9: 144-157.*
Abraham et al., Immunopharmacology of rapamycin, Annu. Rev. Immunol., 14:483-510, 1996.
Battaglia et al., The puzzling world of murine T regulatory cells, Microbes Infection, 4:559-566, 2002.
Belghith et al., TGF-β-dependent mechanisms mediate restoration of self-tolerance induced by antibodies to CD3 in overt autoimmune diabetes, Nat. Med., 9:1202-1208, 2003.
Blaha et al., The influence of immunosuppressive drugs on tolerance induction through bone marrow transplantation with costimulation blockade, Blood, 101:2886-2893, 2003.
Chung et al., Rapamycin-FKBP specifically blocks growth-dependent activation of and signaling by the 70 kd S6 protein kinases, Cell, 69:1227-1236, 1992.

(Continued)

*Primary Examiner* — Amy Juedes
(74) *Attorney, Agent, or Firm* — Marshall, Gerstein & Borun LLP

(57) ABSTRACT

A method for generating/expanding in vitro a $CD4^+CD25^+$ T regulatory (Tr) cell and the use thereof in the treatment of diseases associated with a cell-mediated immune response (including T- and antibody-mediated responses).

31 Claims, 16 Drawing Sheets

(56) References Cited

OTHER PUBLICATIONS

Cortesini et al., The concept of partial clinical tolerance, Transplant Immunol., 13:101-104, 2004.

Davalli et al., Vulnerability of islets in the immediate posttransplantation period: dynamic changes in structure and function, Diabetes, 45:1161-1167, 1996.

Dumont et al., Distinct mechanisms of suppression of murine T cell activation by the related macrolides FK-506 and rapamycin, J. Immunol., 144:251-258, 1990.

Edinger et al., $CD4^+CD25^+$ regulatory T cells preserve graft-versus-tumor activity while inhibiting graft-versus-host disease after bone marrow transplantation, Nat. Med., 9:1144-1150, 2003.

Fehérvari et al., Development and function of $CD25^+CD4^+$ regulatory T cells, Curr. Opin. Immunol., 16:203-208, 2004.

Fingar et al., Mammalian cell size is controlled by mTOR and its downstream targets S6K1 and 4EBP1/eIF4E, Genes Dev., 16:1472-1487, 2002.

Ghobrial et al., Kinetics of in vitro immune responses of T and B cells during tolerance induction by sirolimus, Ann. Transplant., 1:22-29, 1996.

Hackstein et al., Rapamycin inhibits macropinocytosis and mannose receptor-mediated endocytosis by bone marrow-derived dendritic cells, Blood, 100:1084-1087, 2002.

Hering et al., Transplantation of cultured islets from two-layer preserved pancreases in type 1 diabetes with anti-CD3 antibody, Am. J. Transplant., 4:390-401, 2004.

Hojo et al., Cyclosporine induces cancer progression by a cell-autonomous mechanism, Nature, 397:530-534, 1999.

International Preliminary Report on Patentability, PCT/IB2006/001116, dated Aug. 28, 2007.

International Search Report, PCT/IB2006/001116, dated Nov. 30, 2006.

Jones et al., Post-hematopoietic cell transplantation control of graft-versus-host disease by donor CD425 T cells to allow an effective graft-versus-leukemia response, Biol. Blood Marrow Transplant, 9:243-256, 2003.

Kahan et al., Rapamycin: clinical results and future opportunities, Transplantation, 72:1181-1193, 2001.

Kato et al., Cyclic AMP-induced G1 phase arrest mediated by an inhibitor (p27Kip1) of cyclin-dependent kinase 4 activation, Cell, 79:487-496, 1994.

Koenen et al., Superior T-cell suppression by rapamycin and FK506 over rapamycin and cyclosporine A because of abrogated cytotoxic T-lymphocyte induction, impaired memory responses, and persistent apoptosis, Transplantation., 75:1581-1590, 2003.

Levings et al., Human $CD25^+CD4^+$ T suppressor cell clones produce transforming growth factor beta, but not interleukin 10, and are distinct from type 1 T regulatory cells, J. Exp. Med., 196:1335-1346, 2002.

Lyons et al., Determination of lymphocyte division by flow cytometry, J. Immunol. Methods, 171:131-137, 1994.

Morice et al., Rapamycin-induced inhibition of p34cdc2 kinase activation is associated with G1/S-phase growth arrest in T lymphocytes, J. Biol. Chem., 268:3734-3738, 1993.

Nourse et al., Interleukin-2-mediated elimination of the p27Kip1 cyclin-dependent kinase inhibitor prevented by rapamycin, Nature, 372:570-573, 1994.

Powell et al., Inhibition of cell cycle progression by rapamycin induces T cell clonal anergy even in the presence of costimulation, J. Immunol., 162:2775-2784, 1999.

Saunders et al., Rapamycin in transplantation: a review of the evidence, Kidney Int., 59:3-16, 2001.

Schmelzle et al., TOR, a central controller of cell growth, Cell, 103:253-262, 2000.

Sehgal, Rapamune (RAPA, rapamycin, sirolimus): mechanism of action immunosuppressive effect results from blockade of signal transduction and inhibition of cell cycle progression, Clin. Biochem., 31:335-340, 1998.

Taams et al., Immune regulation by $CD4^+CD25^+$ regulatory T cells: implications for transplantation tolerance, Transplant Immunol., 11:277-285, 2003.

Taylor et al., The infusion of ex vivo activated and expanded $CD4^+CD25^+$ immune regulatory cells inhibits graft-versus-host disease lethality, Blood, 99:3493-3499, 2002.

Terada et al., Failure of rapamycin to block proliferation once resting cells have entered the cell cycle despite inactivation of p70 S6 kinase, J. Biol. Chem., 268:12062-12068, 1993.

Terada et al., Rapamycin inhibits ribosomal protein synthesis and induces G1 prolongation in mitogen-activated T lymphocytes, J. Immunol., 155:3418-3426, 1995.

Thornton et al., Suppressor effector function of $CD4^+CD25^+$ immunoregulatory T cells is antigen nonspecific, J. Immunol., 164:183-190, 2000.

Tian et al., Acceleration of apoptosis in $CD4^+CD8^+$ thymocytes by rapamycin accompanied by increased $CD4^+CD25^+$ T cells in the periphery, Transplant Immunol., 77:183-189, 2004.

Trenado et al., Recipient-type specific $CD4^+CD25^+$ regulatory T cells favor immune reconstitution and control graft-versus-host disease while maintaining graft-versus-leukemia, J. Clin. Invest., 112:1688-1696, 2003.

Vu et al., Different costimulatory and growth factor requirements for $CD4^+$ and $CD8^+$ T cell-mediated rejection, J. Immunol., 173:214-221, 2004.

Wells et al., Requirement for T-cell apoptosis in the induction of peripheral transplantation tolerance, Nat. Med., 5: 1303-1307, 1999.

Written Opinion of the International Searching Authority, PCT/IB2006/001116, dated Nov. 30, 2006.

You et al., Autoimmune diabetes onset results from qualitative rather than quantitative age-dependent changes in pathogenic T-cells, Diabetes, 54:1415-1422, 2005.

\* cited by examiner

CD4⁺CD25⁺

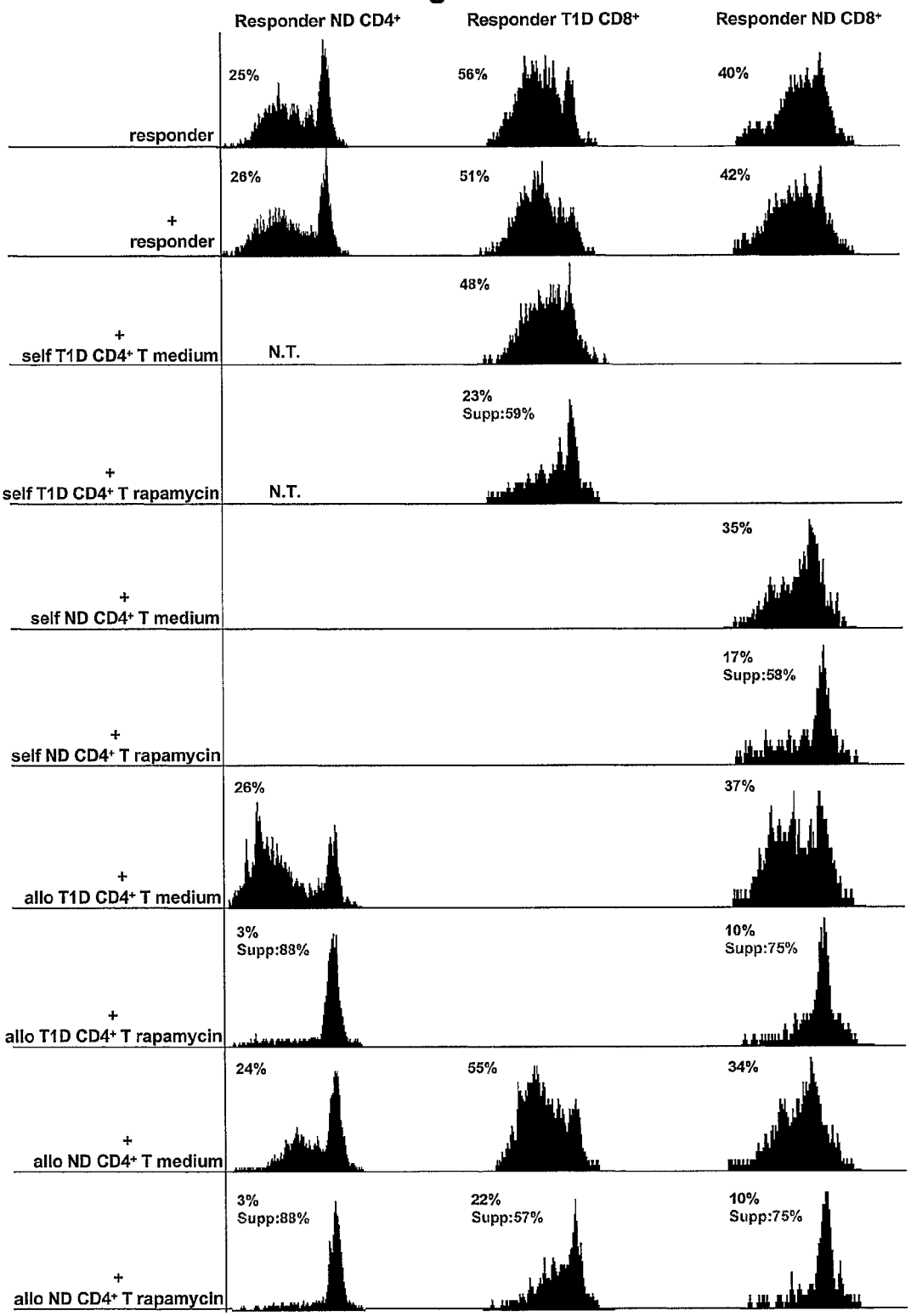

B

METHOD FOR EXPANDING CD4+ CD25+ T REGULATOR CELLS

FIELD OF THE INVENTION

The present invention relates to methods for generating/expanding in vitro a $CD4^+CD25^+$ T regulatory (Tr) cell or population and the use of such a cell or population for the treatment of diseases associated with a cell-mediated immune response (including T- and antibody-mediated immune responses). The present invention also relates to methods of eliminating/reducing a $CD4^+CD25^-$ T effector cell or a population thereof.

BACKGROUND OF THE INVENTION

The modulation of cell-mediated immune responses (including T- and antibody-mediated immune responses) is important in a therapeutic context.

Organ and cell transplantation is the treatment of choice for most patients with end stage kidney-failure, heart or liver disease, autoimmune type 1 diabetes and it is a developing possibility for patients with deficiencies in small-bowel function. Graft survival depends on a number of factors but the most significant of these is the administration of powerful immunosuppressive drugs. Transplantation between genetically disparate individuals evokes a rapid and potentially destructive alloreactive immune response that, if left uncontrolled, can lead to complete destruction of the transplanted organ or to graft versus host disease (GVHD). Administration of immunosuppressive drugs attenuates this response and thus prevents acute graft rejection. However, continued graft survival depends on life-long or prolonged immunosuppression because withdrawal of immunosuppression results in re-activation of the rejection response, leading to rapid graft destruction.

Although the currently available immunosuppressive drugs are very effective in short term, substantial problems indicate a pressing need to develop alternative and more sophisticated ways of preventing graft rejection. The main obstacle is the inability to distinguish between beneficial immune responses against infectious pathogens and destructive immune responses against the graft. Thus, immunosuppressive therapies can lead to increased risk of opportunistic infections. Several studies show that non-specific immunosuppression would lead to an increased incidence of cancer in transplanted patients (Hojo 1999). Therefore, the full potential of transplantation will be realised only when alternatives to non-specific immunosuppression will be found. The major aim of transplantation immunology is to develop protocols that prevent immune responses towards the graft but leave the rest of the immune system intact. This accomplishment will lead to transplantation tolerance.

In autoimmune diseases, undesired immune responses to self-antigens lead to destruction of peripheral tissues. Treatments of autoimmune diseases are currently based on down-modulation of inflammation and non-antigen (Ag) specific immunosuppression. As for prevention of allograft rejection, this strategy is frequently not effective in the long term with high risk of relapse once the drug is withdrawn and hazards of excessive immunosuppression, including infections and tumors. The alternative approach is based on the induction of transient immunosuppression and/or specific immune tolerance, aimed at "silencing" the pathogenic response to self-Ag, while keeping host defense mechanisms intact.

The immune system has evolved two distinct mechanisms to induce tolerance to self or non-harmful antigens. These are referred to as central and peripheral T cell tolerance. Central tolerance is realized during fetal development and the very early natal period and is mediated by clonal deletion of self-reactive T cells during thymic development. Peripheral mechanisms induce tolerance in mature T cells and occur in the periphery during the whole life. These mechanisms include functional inactivation of antigen specific lymphocytes (named anergy) and activation of T cell subsets with suppressive and regulatory capacities (reviewed in Battaglia 2002).

Recently, there has been a growing interest in the induction of T regulatory (Tr) cells as a strategy to achieve immunological tolerance. The majority of Tr cells identified to date lie within the $CD4^+$ population, and the $CD4^+$ Tr cells that constitutively express the $IL-2R\alpha$ chain (CD25) are one of the best characterized so far both in mouse and humans. Our invention concentrates on this Tr cell subset identified as $CD4^+CD25^+$ Tr cells.

SUMMARY OF THE INVENTION

Rapamycin is an immunosuppressive compound that, by binding the mammalian target of rapamycin (mTOR), inhibits cytokines induced T-cell proliferation (Sehgal 1998). Rapamycin is currently used to prevent acute graft rejection in humans, and has been shown to allow operational tolerance in murine models of transplantation (Blaha 2003). However, a direct effect of rapamycin on Tr cells, which play a key role in the induction and maintenance of peripheral tolerance, has not been demonstrated so far. We have now found that rapamycin selectively expands or promotes the naturally occurring $CD4^+CD25^+$ Tr cells in vitro. Thus, rapamycin can be used to generate/expand $CD4^+CD25^+$ Tr cells for ex-vivo cellular therapy in T cell-mediated diseases.

We have found that in vitro treatment of $CD4^+$ T cells, which includes both $CD4^+CD25^+$ Tr cells (5-10% of the total $CD4^+$ T cells) and T effector cells, with rapamycin increases by 20 fold the $CD4^+CD25^+$ Tr cell content.

The ability of rapamycin to selectively expand $CD4^+CD25^+$ Tr cells in such large amounts may be limited to the in vitro approach.

We have also found that rapamycin in vitro selectively eliminates $CD4^+CD25^-$ T effector cells from a population of T cells comprising both such T effector cells and $CD4^+CD25^+$ Tr cells.

STATEMENTS OF THE INVENTION

According to one aspect of the present invention there is provided a method for producing, including culturing, a $CD4^+CD25^+$ T regulatory (Tr) cell comprising incubating a T cell or T cell population obtained from a human or animal with rapamycin or a derivative thereof.

According to another aspect of the present invention there is provided a method for generating or expanding the population of $CD4^+CD25^+$ Tr cells in a population of T cells comprising incubating the population of T cell obtained from a human or animal with rapamycin or a derivative thereof.

Thus, we have found that rapamycin or a derivative thereof allows the culturing of, promotes expansion or proliferation of functional $CD4^+CD25^+$ Tr cells and in particular $CD4^+CD25^+FOXP3^+$ Tr cells.

By "functional $CD4^+CD25^+$ Tr cells", we mean that the $CD4^+CD25^+$ Tr cells retain their suppressive activity and/or that the $CD4^+CD25^+$ Tr cells maintain expression of regulatory markers such as FOXP3.

According to another aspect of the present invention, there is provided a method for selectively eliminating or reducing the number of CD4+CD25− T cells in a population of T cells comprising incubating the population of T cells obtainable from a human or animal with rapamycin or a derivative thereof.

In other words, rapamycin selectively blocks T cell receptor-(TCR) mediated proliferation of CD4+CD25− T cells, but not of CD4+CD25+ Tr cells.

Whilst not wishing to be bound by any theory it is believed that CD4+CD25+ Tr cells may undergo less apoptosis that CD4+CD25− T effector cells in the presence of rapamycin. Alternatively or in addition, rapamycin may block the sensitivity of the T effector cells to IL-2, so that they do not expand.

It is believed that tumor cell-based therapies such as vaccines and bone marrow transplants can induce potent, tumor-specific immune disease relapse, the most significant post-transplant complication. Unlike the patient's T cells, which are often functionally impaired by the cancer or its treatment, donor T cells are fully functional and are more likely to mount significant response to the therapy. The present invention may be advantageous since culturing with rapamycin reduces risks associated with T effector cells when T cells are donated to a patient.

In one embodiment, the CD4+CD25+ Tr cell produced according to the present invention is (re-) introduced into a patient alone or in combination with a drug.

In one embodiment the T cell is a naïve T cell.

Preferably the T cell is activated.

In one embodiment the method further comprises incubating in the presence of a cytokine. Preferably the cytokine is IL-2.

In one embodiment the method further comprises incubating in the presence of antigens, including allergens, alloantigens, self-antigens, food antigens, and microbial antigens.

According to another aspect of the present invention there is provided a CD4+CD25+ Tr cell produced by the method of the invention.

According to another aspect of the present invention there is provided use of a CD4+CD25+ Tr cell according to the present invention for the modulation of a cell-mediated immune response.

According to yet another aspect of the present invention there is provided a pharmaceutical composition comprising the CD4+CD25+ Tr cell according to the present invention and a pharmaceutically acceptable carrier, excipient or diluent.

According to a further aspect of the present invention there is provided use of a CD4+CD25+ Tr cell according to the invention for the preparation of a medicament for the treatment of a disease associated with a cell-mediated immune response.

In previous experiments with type I diabetes, it was reported that T regulatory cells did not give rise to immune suppression. However, surprisingly therefore we have found that cell-based treatment can be effective using the method of the present invention. It may be that the previous experiments did not give rise to immune suppression due to the presence of T effector cells, which are eliminated using the present invention.

DETAILED DESCRIPTION OF THE INVENTION

Various preferred features and embodiments of the present invention will now be described by way of non-limiting example.

Although in general the techniques mentioned herein are well known in the art, reference may be made in particular to Sambrook et al., Molecular Cloning, A Laboratory Manual (1989) and Ausubel et al., Short Protocols in Molecular Biology (1999) 4th Ed, John Wiley & Sons, Inc (as well as the complete version Current Protocols in Molecular Biology).

Rapamycin, a macrolide antibiotic produced by *Streptomyces hygroscopicus*, is a new effective drug used to prevent allograft rejection (Kahan 2001). Similarly to the immunosuppressants FK506 and cyclosporin A (CsA), rapamycin exerts its effect by binding to the intracellular immunophilin FK506 binding protein (FKBP12). However, unlike FK506 and CsA, rapamycin does not inhibit TCR-induced calcineurin activity. Rather, the rapamycin-FKBP12 complex inhibits the serine/threonine protein kinase called mTOR (mammalian target of rapamycin), which activation is required for protein synthesis and cell cycle progression. Therefore, rapamycin blocks signaling in response to cytokines/growth factors, whereas FK506 and CsA exert their inhibitory effects by blocking TCR-induced activation (reviewed in Abraham 1996). A direct effect of rapamycin on Tr has not been demonstrated so far.

This invention provides an ex vivo method of treating or preventing cell-mediated diseases in a mammal in need thereof, which comprises the use of a rapamycin. As defined herein, the term "a rapamycin" defines a class of immunosuppressive compounds which contain the basic rapamycin nucleus (shown below). The rapamycins of this invention include compounds which may be chemically or biologically modified as derivatives of the rapamycin nucleus, while still retaining immunosuppressive properties.

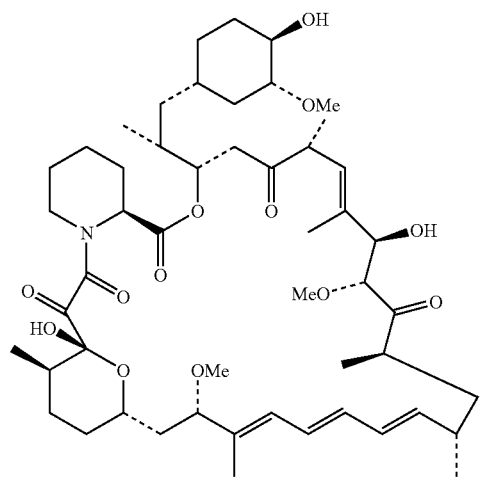 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

Accordingly, the term "a rapamycin" includes esters, ethers, oximes, hydrazones, and hydroxylamines of rapamycin, as well as rapamycins in which functional groups on the rapamycin nucleus have been modified, for example through reduction or oxidation. The term "a rapamycin" also includes pharmaceutically acceptable salts of rapamycins, which are capable of forming such salts, either by virtue of containing an acidic or basic moiety.

It is preferred that the esters and ethers of rapamycin are of the hydroxyl groups at the 42- and/or 31-positions of the rapamycin nucleus, esters and ethers of a hydroxyl group at the 27-position (following chemical reduction of the 27-ketone), and that the oximes, hydrazones, and hydroxylamines are of a ketone at the 42 position (following oxidation of the 42-hydroxyl group) and of 27-ketone of the rapamycin nucleus.

Preferred 42- and/or 31-esters and ethers of rapamycin are disclosed in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl ethers (U.S. Pat. No. 5,120,842); aminoesters (U.S. Pat. No. 5,130,307); acetals (U.S. Pat. No. 551,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamate (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); 0-alkyl ethers (U.S. Pat. No. 5,665,772); and PEG esters of rapamycin (U.S. Pat. No. 5,780,462). The preparation of these esters and ethers is disclosed in the patents listed above.

Accordingly examples of rapamycin compounds include compounds of formula:

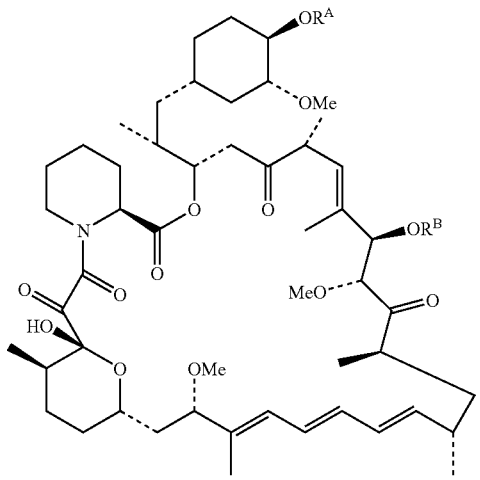

Wherein RA and RB are each selected from hydrogen and ester or ether forming groups as disclosed in any one of the abovementioned U.S. patents.

Preferred 27-esters and ethers of rapamycin are disclosed in U.S. Pat. No. 5,256,790, which is hereby incorporated by reference. The preparation of these esters and ethers is disclosed in the aforementioned patent.

Preferred oximes, hydrazones, and hydroxylamines of rapamycin are disclosed in U.S. Pat. Nos. 5,373,014, 5,378,836, 5,023,264, and 5,563,145, which are hereby incorporated by reference. The preparation of these oximes, hydrazones, and hydroxylamines is disclosed in the above listed patents. The preparation of 42 oxorapamycin is disclosed in U.S. Pat. No. 5,023,263, which is hereby incorporated by reference.

Particularly preferred rapamycins include rapamycin [U.S. Pat. No. 3,929,992], rapamycin 42-ester with 3-hydroxy-2-(hydroxymethyl)-2-methylpropionic acid [U.S. Pat. No. 5,362,718], and 42-0-(2-hydroxy) ethyl rapamycin [U.S. Pat. No. 5,665,772].

When applicable, pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when the rapamycin contains a suitable basic moiety. Salts may also be formed from organic and inorganic bases, such as alkali metal salts (for example, sodium, lithium, or potassium) alkaline earth metal salts, ammonium salts, alkylammonium salts containing 1-6 carbon atoms or dialkylammonium salts containing 1-6 carbon atoms in each alkyl group, and trialkylammonium salts containing 1-6 carbon atoms in each alkyl group, when the rapamycin contains a suitable acidic moiety.

T Regulatory (Tr) Cells

Tr cells are well characterized T cell subsets, which play a key role in inducing and maintaining immunological tolerance. Among the CD4$^+$ Tr cells, the Tr cell subset that express the IL-2Rα chain (CD4$^+$CD25$^+$) is one of the most extensively characterized so far (reviewed in Fehervari 2004). CD4$^+$CD25$^+$ Tr cells are generated in the thymus and are part of the normal peripheral T cell repertoire. Suppressive CD4$^+$CD25$^+$ Tr cells can be distinguished from activated T cells based on the high constitutive expression of CD25, CTLA-4, GITR, and the transcription factor FOXP3. Once generated, thymic CD4$^+$CD25$^+$ Tr cells migrate to peripheral tissues, where they potently suppress proliferation and cytokine production by both CD4$^+$ and CD8$^+$ T cells via a mechanism that requires cell-cell contact (Fehervari 2004). CD4$^+$CD25$^+$ Tr cells contribute to tolerance induction after solid organ transplantation and protect from graft versus host disease (GVHD) lethality in bone marrow transplantion models (Taams 2003). Moreover, it has been demonstrated that CD4$^+$CD25$^+$ Tr cells play important immunomodulatory roles in several animal models of autoimmunity, allergy, and infection (Fehervari 2004).

Here we provide evidence that in vitro exposure of CD4$^+$ T cells to rapamycin induces expansion of the naturally occurring CD4$^+$CD25$^+$FOXP3$^+$ Tr cells, which retain their suppressive functions in vitro and in vivo.

Preparation of Primed T Cells In Vitro

A population of T cells for use in the present invention may be obtained from peripheral blood or secondary lymphoid organs. The T cells may also be obtained from a sample using α-CD4$^+$ monoclonal antibody-coated microbeads. In one embodiment the T cells are further purified using α-CD25$^+$ monoclonal antibody-coated microbeads. The T cells may also be obtained from a sample using flow cytometry (FACS). T cells may be cultured in a suitable culture medium such as X-VIVO, optionally in the presence of human serum. Cytokines, such as IL2, may be added. Polyclonal activation of T cells may be induced with α-CD3 and α-CD28 antibodies. Alternatively or in addition, an antigen or allergen of interest may be added. The T cells are generally co-cultured with antigen presenting cells (APCs). However, it may be preferred to prepare primed APCs first and then incubate them with T cells. The rapamycin is then typically added to the culture. The allergen or antigen may be added before, after or at substantially the same time as the rapamycin.

In one embodiment, the T cells are incubated with rapamycin over a period of around 1-4 weeks, preferably around three weeks. Rapamycin may be added to the medium over the period of this incubation, e.g., once a week. As an example, rapamycin may be added in an amount of around 100 nM.

Therapeutic Uses

The present invention may be used in association with organ transplantation, such as kidney, heart, liver, islet or bone marrow transplantation, and in the treatment or prevention of graft-versus-host disease. For example, in bone marrow allogeneic transplant it has been demonstrated that ex vivo expanded alloantigen specific $CD4^+CD25^+$ Tr cells control graft versus host disease (GVHD), while allow reconstitution of the immune system post-transplantation (Taylor 2002, Trenado 2003, Edinger 2003). $CD4^+CD25^+$ Tr cells may also be able to modulate GVHD whilst preserving the graft versus tumor (GVT) or graft versus leukemia (GVL) effect.

In more detail, minor histocompatibility antigens (mHags) are immunogenic peptides from polymorphic cellular proteins that induce strong T-cell responses after human leukocyte antigen (HLA)-matched, mHag-mismatched stem-cell transplantation mHags with broad or limited tissue expression are target antigens for graft versus host (GVH) and graft versus leukemia (GVL) reactivities-Separation of these activities is crucial for adoptive immunotherapy of leukemia without GVH disease.

Recent data suggest that patients with autoimmune diseases, such as diabetes, multiple sclerosis, and rheumatoid arthritis might have defective or reduced number of $CD4^+CD25^+$ Tr cells. Thus, ex vivo cellular therapy to increase the Tr cell compartment is highly encouraged.

Particular conditions associated with autoimmune diseases which may be treated, include: autoimmune (Hasimoto's) thyroiditis, hyperthyroidism (Graves' disease) type I diabetes mellitus, insulin resistant diabetes, autoimmune adrenal insufficiency (addison's disease), autoimmune oophoirits, autoimmune orchitis, autoimmune hemolytic anemia, paroxysmal cold hemoglobinuria, autoimmune thrombocytopenia, autoimmune neutropenia, pernicius anemia, pure red cell anemia, autoimmune coagulopathies, myasthenia gravis, autoimmune polyneuritis, multiple sclerosis, experimental allergic encephalomyelitis, pemphigus and other bullous diseases, rheumatic carditis, Goodpasture's syndrome, postcardiotomy syndrome, systemic lupus erythematosus, rheumatoid arthritis, Sjorgen's syndrome, polymyositis, dermatomyositis, scleroderma; inflammatory bowel diseases: Chron's disease, ulcerative colitis; chronic obstructive pulmonary diseases; chronic inflammatory diseases; allergic diseases: asthma, atopic dermatitis; fibrotic diseases; and immune reactions to gene therapy derived products.

The present invention also envisages manipulating the expanded cells, for example through cytokine stimulation or by adding genes or interest—such as therapeutic genes or knock-out genes, prior to administration to a patient.

As the present invention provides a method for expanding the CD4+CD25+ T cells it provides a useful tool for readily investigating their function and cell surface markers. Thus, the present invention further envisages the use of the expanded cells in assays.

Administration

The present invention provides a method of using expanded Tr cells in cellular therapy. Tr cells from a patient could be isolated and expanded in vitro, and then re-administered to the patient. In another embodiment, Tr cells could be obtained from a donor. Preferably the cells are reinfused into the patient.

Tr cells of the present invention for use in immunotherapy are typically formulated for administration to patients with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, intra-peritoneal, injection, intranasal inhalation, lung inhalation, intradermal, intra-articular, intrathecal, or via the alimentary tract (for example, via the Peyers patches).

Cells and pharmaceutical comprising cells of the invention are typically administered to the patient by intramuscular, intraperitoneal or intravenous injection, or by direct injection into the lymph nodes of the patient, preferably by direct injection into the lymph nodes.

Typically from $10^4$/kg to $10^9$/kg treated cells, preferably from $10^5$/kg to $10^7$/kg cells, more preferably about $10^6$/kg cells are administered to the patient.

The routes of administration and dosages described are intended only as a guide since a skilled practitioner will be able to determine readily the optimum route of administration and dosage for any particular patient depending on, for example, the age, weight and condition of the patient.

EXAMPLES

Figure 1A:
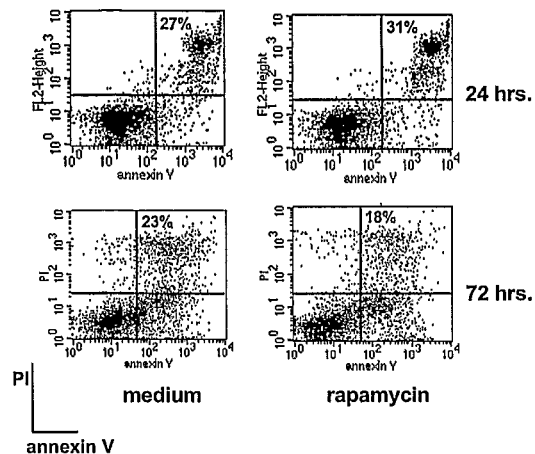
FIG. 1 shows the results of Example 1.

Material and Methods for Examples 1 and 2

Mice.

Balb/c, C57BL/6, and DO11.10 (TCR tg specific for OVA) female mice were purchased from Charles River Laboratories (Calco, Italy). All mice were kept under specific pathogen free conditions.

Flow Cytometry and Cell Sorting.

Cells were stained with the indicated Abs (all from BD Biosciences, Mountain View, Calif.), and were analyzed with a FACScan flow cytometer equipped with CellQuest software (BD Biosciences). To obtain highly purified $CD4^+CD25^{+/-}$ T cells, $CD4^+$ T cells were first purified from splenocytes isolated from Balb/c mice by positive selection with αCD4 mAb-coated microbeads (Miltenyi Biotec, Bergisch Gladbach, Germany). Thereafter, $CD4^+$ T cells were stained with Cy-coupled αCD4 and PE-coupled αCD25 mAbs (BD Biosciences) and $CD4^+CD25^+$ T cells were sorted by FACS-sorting on a FAC-Star (BD Biosciences).

T Cell Cultures.

$CD4^+$ T cells were obtained by incubation of splenocytes with αCD4 mAb-coated microbeads and applied onto Mini-Macs columns (Miltenyi Biotec). The average purity was 95%.

$1\times10^6$ $CD4^+$ T cells isolated from spleen of DO11.10 tg mice were stimulated with $4\times10^6$ APC from Balb/c mice (i.e. total splenocytes irradiated 3000 Rad) and 0.6 μM OVA$_{323-339}$peptide (OVA) (Primm, Milano, Italy). Three rounds of stimulation of 7 days each were performed. IL-2 (BD Biosciences) was added starting from the second round of stimulation at 50 U/ml. Alternatively, 1×10$^6$ CD4$^+$ T cells isolated from spleen of Balb/c mice were stimulated with coated 10 μg/ml of αCD3 and soluble 1 μg/ml of αCD28 mAbs (BD Biosciences). Cells were cultured in the presence of medium alone or 100 nM rapamycin (Sigma, St Louis, Mo.). Three rounds of stimulation of 7 days each were performed. IL-2 (BD Biosciences) was added starting from the second round of stimulation at 50 U/ml. In separate experiments, sorted CD4$^+$CD25$^+$ T cells isolated from spleen of Balb/c mice were stimulated with coated 10 μg/ml of αCD3, soluble 1 μg/ml of αCD28 mAbs (BD Biosciences) and 1000 U/ml of IL-2. Cells were cultured in the presence of medium alone or 100 nM rapamycin (Sigma, St Louis, Mo.). 1000 U/ml of IL-2 was added at the beginning of each new stimulation.

FOXP3 Quantitative PCR.

Total RNA was extracted with Eurozol (Euroclone, Switzerland), and cDNA was synthesized with High Capacity cDNA Archive Kit (Applied Biosystems, New Jersey, USA). Levels of FOXP3 mRNA was quantified using Assay on Demand real-time PCR kits (Applied Biosystems, New Jersey, USA) with TaqMan Universal PCR Master Mix (Applied Biosystems, New Jersey, USA). Levels of 18s rRNA was quantified as internal control by using TaqMan PDAR Eukaryotic 18s Endogenus Controls (Applied Biosystems, assay ID: Mm00475156m1). Samples were run in duplicate, and relative expression of FOXP3 was determined by normalizing to 18 s expression in each set of samples in order to calculate a fold-change in value.

Suppression Experiments.

CD4$^+$ T cells isolated from naïve Balb/c mice or KJ1-26$^+$ (αOVA-specific TCR) T cells isolated from DO11.10 tg mice were stained with CFSE (Molecular Probes) as described elsewhere (Lyons 1994) and cultured in 96 well plates (2×10$^5$/well) coated with 10 μg/ml αCD3 mAb (BD Biosciences) or irradiated splenocytes and OVA. T cells cultured for 3 weeks in medium or rapamycin were added in 1:1 ratio (i.e. 10$^5$:10$^5$) to the culture, and 5 days later the cells were collected and analyzed by FACS. The percentage of CFSE$^+$ cells divided in the presence of cultured cells was compared to percentage of CFSE$^+$ divided cells in the absence of any added cells.

In the transwell experiments, CD4$^+$ T cells isolated from naïve Balb/c mice were stained with CFSE (Molecular Probes) and cultured at the bottom of 48 transwell plates (5×10$^5$/well) coated with 10 μg/ml αCD3 mAb (BD Biosciences). On top of the transwell were seeded T cells cultured for 3 weeks in medium or rapamycin in 1:1 ratio, pre-activated with αCD3 mAb for 6 hours. After 5 days of culture, cells from the bottom compartment were collected and analyzed by FACS.

Cell Proliferation by CFSE Analysis.

The proportion of CFSE$^+$ cells proliferating in vitro was calculated as described elsewhere (Lyons 1994). Briefly, the number of cells (events) in a given cycle (division: n) was divided by 2 raised to power n, to calculate the percentage of original precursor cells from which they arose. The sum of original precursors from division 1 to 6 represents the number of precursors cells which proliferated. The percent of CFSE$^+$ divided cells was calculated by [(# of precursors that proliferated$_{1-6}$/# of total precursors$_{0-6}$)×100].

Islet Transplant.

Diabetes was induced in Balb/c mice by intravenous injection of streptozotocin (Sigma, St. Louis, Mo.) at 170 mg/kg. A diagnosis of diabetes was made after two sequential glucose measurements higher than 350 mg/dl. Hand picked pancreatic β-islets isolated from C57BL/6 were transplanted under the kidney capsule of recipient Balb/c diabetic mice, as previously described (Davalli 1996).

Statistical Analysis.

All statistical analyses were performed using the Student t-test. Kaplan Meier survival curves were compared by the log-rank test.

Example 1

Rapamycin does not Block Activation Induced Cell Death and Proliferation of Murine CD4$^+$ T Cells To define the effect of rapamycin on T cells, naïve CD4$^+$ T cells from spleens of DO11.10 TCR tg mice were activated with APC+OVA in the presence or absence of rapamycin and activation induced cell death (AICD) was monitored by binding of annexin V. In cells exposed to rapamycin, neither increase nor reduction of apoptosis was observed upon in vitro activation, compared to control cells (FIG. 1A). In more detail, DO11.10 tg CD4$^+$ T cells were cultured with APC+OVA (medium) or APC+OVA+rapamycin (rapamycin) and AICD was monitored by FACs after 24 and 72 hours of culture. Percentage of PI$^+$-annexinV$^+$ cells is indicated in each dot plot. These results confirm that rapamycin does not prevent AICD in CD4$^+$ T cells as already demonstrated in murine splenic mononuclear leukocytes activated with αCD3 mAb (Wells 1999), and in human peripheral blood mononuclear cells activated in primary mixed lymphocyte cultures (Koenen 2003).

Figure 1B:
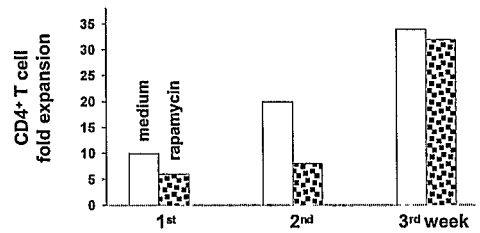

To define the effects of a long-term exposure of T cells to rapamycin, naïve CD4$^+$ T cells from DO11.10 TCR tg mice were activated in vitro with APC+OVA for three consecutive weeks in the presence or absence of rapamycin. Fold expansion of T cells was determined after each round of stimulation. As shown in FIG. 1B, fold expansion of DO11.10 tg CD4$^+$ T cells 1, 2, and 3 weeks after culture in the presence of APC+OVA (medium, white bars) or APC+OVA+rapamycin (rapamycin, dotted bars) was evaluated by direct cell counts. T cells activated in the presence of rapamycin had a delayed kinetic of proliferation compared to control cells. However, at the end of the third week of culture the same number of T cells was recovered in control- and rapamycin-cultures (FIG. 1B). Rapamycin binds to FKBP12 and the formed complex inhibits the function of mTOR, which is involved in a broad range of physiological processes linked to the control of cell-cycle. Indeed, rapamycin is widely considered as an inhibitor of T cell cycle by arresting T cells in G$_1$ phase (Dumont 1990, Chung 1992, Morice 1993, Nourse 1994, Kato 1994). Based on this mode of action, rapamycin is used as an immunosuppressive agent for the treatment of transplant rejection. However, patients who received rapamycin did not reveal higher susceptibility to infections, as expected by general immunosuppression (Saunders 2001). Furthermore, it has been demonstrated that rapamycin has some effects in blocking CD4$^+$ T cell cycle entry, but the majority of the cells, once enter the cell cycle, are perfectly capable of dividing (Terada 1993, Terada 1995, Vu 2004). In line with these observations, our results demonstrate that rapamycin does not block CD4$^+$ T cells expansion.

Figure 1C:
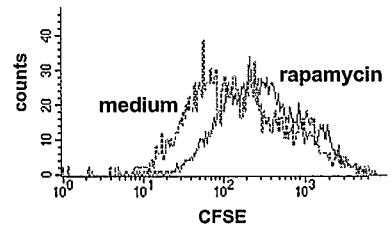

After one, two (data not shown), or three rounds of stimulation (FIG. 1C), CD4$^+$ T cells activated in the presence of rapamycin and re-stimulated with APC+OVA in the absence of rapamycin, retained their ability to proliferate, although the overall number of cell divisions was slightly reduced. In more detail in relation to FIG. 1C, after 3 rounds of stimulation with APC+OVA (medium) or APC+OVA+rapamycin (rapamycin), DO11.10 tg CD4$^+$T cells were stained with CFSE and re-stimulated with APC+OVA in the absence of the compound and of exogenous IL-2. CFSE dilution was monitored 5 days after activation.

These data indicate that exposure to rapamycin does not induce anergy in CD4$^+$ T cells. These results are in line with those reported in vitro by Koenen et al. (2003) and in vivo by Ghobrial et al. (1996), but are in contrast with the findings of Powell and colleagues who showed that a Th1 cell clone responding to APC+Ag become anergic when treated with rapamycin (Powell 1999). One possible explanation for the observed differences might be that, in the aforementioned study a murine CD4$^+$ T cell clone stimulated with APC+Ag and rapamycin overnight was tested, whereas in our experimental model we used a polyclonal T cell population activated in an Ag-specific way for three times in the presence of rapamycin.

Figure 1D:
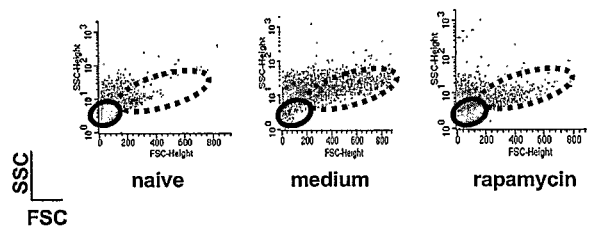

Although T cells repetitively activated in vitro for three weeks in the presence of rapamycin proliferated similarly to control cells, rapamycin-exposed CD4$^+$ T cells were smaller and displayed a more round-like shape than control cells (FIG. 1D). After 3 rounds of stimulation with APC+OVA (medium) or APC+OVA+rapamycin (rapamycin), DO11.10 tg CD4$^+$ T cells were left resting for one additional week with no further stimulation in the presence of IL-2 (50 U/ml). At the end of the seven days cell size was analyzed by FACS by plotting FSC vs SSC parameters. Small (continuous line) and big (dotted line) cells are circled. Naïve CD4$^+$ T cells from a DO11.10 tg mouse were used as control.

Studies performed in model genetic organisms suggest that cell division and cell growth are normally coordinated yet separable processes and that cells progress through the cell cycle only when sufficient mass, size, and biosynthesis have been reached (reviewed in Schmelzle 2000). On the contrary, Fingar and colleagues demonstrated that cell growth and cell cycle progression are separable processes in mammalian cells and that growth to appropriate cell size requires mTOR-dependent signals. In this study it was demonstrated that inhibition of mTOR is the mechanism by which rapamycin reduces cell size in rat fibroblasts and human osteosarcoma cell lines (Fingar 2002). In line with these findings, our data provide evidence that rapamycin blocks CD4$^+$ T cells growth while allows their proliferation.

Example 2

Rapamycin Expands CD4$^+$CD25$^+$FOXP3$^+$ Tr Cells with Suppressive Ability In Vitro After 3 rounds of stimulation with APC+OVA (medium) or APC+OVA+rapamycin (rapamycin), DO11.10 tg CD4$^+$ T cells were left resting for one week with no further stimulation in the presence of IL-2 (50 U/ml). After seven days cells were analyzed by FACS. Cells were gated on CD4$^+$CD25$^+$ cells and numbers represent percentages of the three different CD25$^+$ subset (i.e. bright, dim, and low). Naïve CD4$^+$ T cells from a DO11.10 tg mouse were used as control.

Content of CD$_{25}^{bright}$ T cells in medium- and rapamycin-cultures in each of the 6 experiments is presented. Star indicates statistical significance (*$0.001<p\leq0.05$).

Figure 2A:
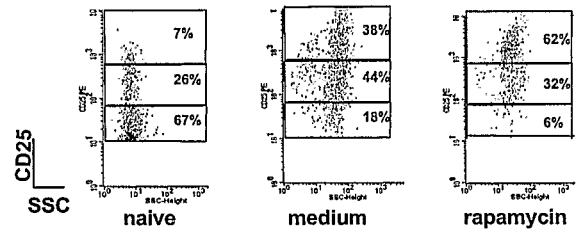
FIGS. 2-7 show the results of Example 2.
Figure 2B:
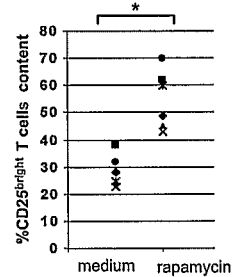

T cells activated in the presence of rapamycin were highly enriched in CD4$^+$CD25$^{bright}$ T cells, which represent the Tr subset among the CD4$^+$CD25$^+$ T cell population (FIGS. 2A and B) (Levings 2002, Belghith 2003).

Figure 2C:
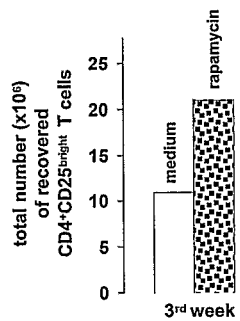

$1\times10^6$ DO11.10 tg CD4$^+$ T cells (containing 70.000 CD$_4^+$CD25$^{bright}$ T cells) were cultured with APC+OVA (medium, white bar) or APC+OVA+rapamycin (dotted bar, rapamycin). After 3 rounds of stimulation, the total number of CD4$^+$CD25$^{bright}$T cells was determined by FACS. Accordingly, the total number of CD4$^+$CD25$^{bright}$ T cells recovered after three weeks of culture and repetitive Ag-stimulation in the presence of rapamycin was markedly superior to that of control cultures (FIG. 2C).

Figure 3A:
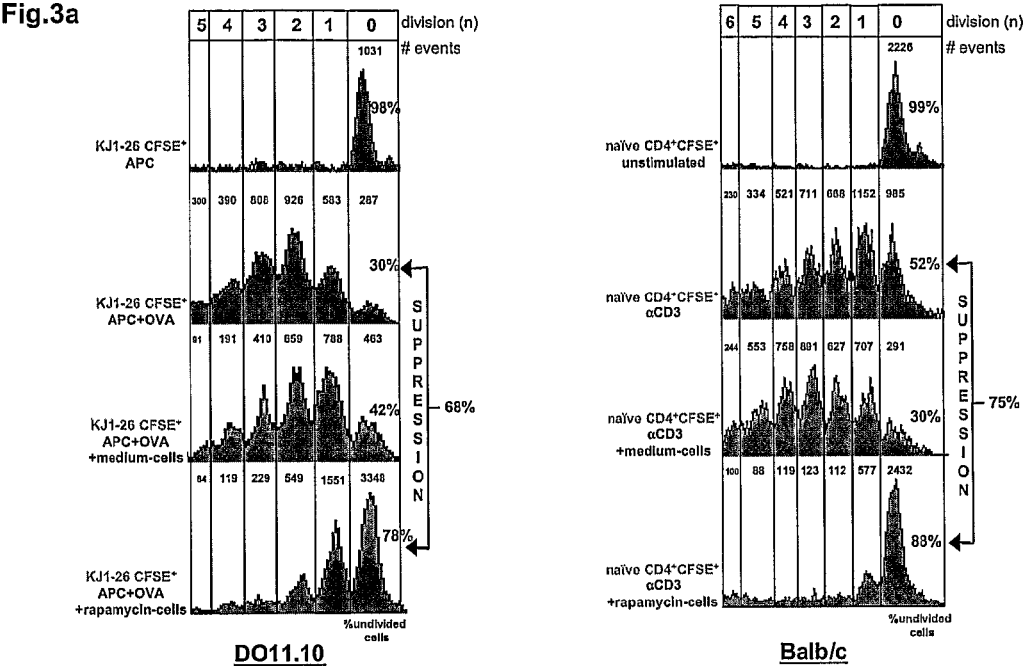
Figure 3B:
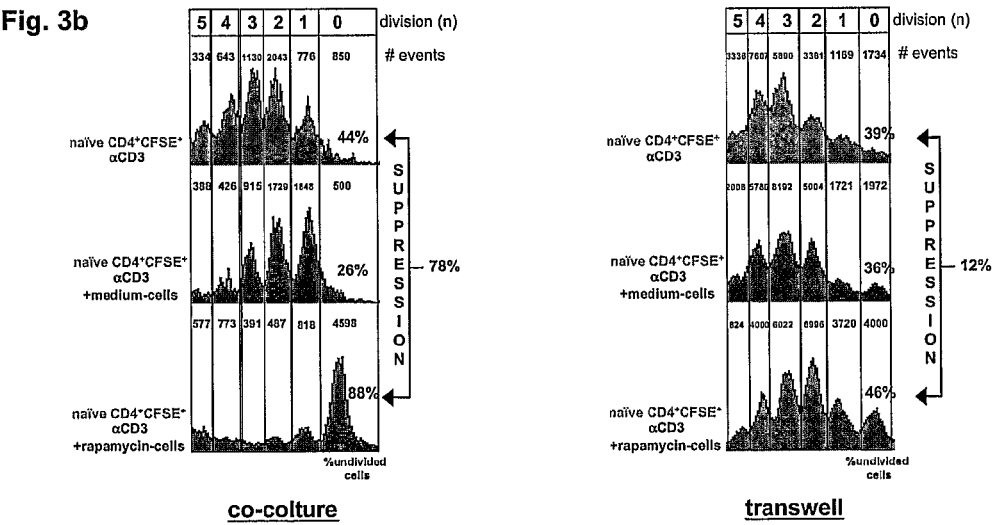

Interestingly, rapamycin-exposed CD4$^+$ T cells were able to suppress proliferation of syngeneic naïve CD4$^+$ T cells activated in vitro with APC+OVA (FIG. 3A, left panel). These data clearly indicate that, although cells exposed to rapamycin are not an homogeneous population and contain around 60% of CD4$^+$CD25$^{bright}$ Tr cells (FIG. 2A), they display a strong suppressive capacity in vitro.

It has been demonstrated that rapamycin profoundly affects the phenotype and function of dendritic cells by reducing their Ag uptake capacity, thereby favoring the differentiation of tolerogenic APC (Hackstein 2002). Thus, the presence of Tr cells in rapamycin-exposed T cell cultures could be due to an indirect effect of rapamycin on APC, which become tolerogenic and induce a Tr cell population, rather than a direct effect on the T cells. To test this hypothesis, we investigated the effects of long-term exposure of T cells to rapamycin in an "APC-free" system. Naïve CD4$^+$ T cells from spleens of Balb/c mice were repetitively activated in vitro with αCD3 and αCD28 mAbs for three weeks in the presence or absence of rapamycin. As demonstrated for T cells activated with APC+OVA, T cells activated with αCD3 and αCD28 mAbs in the absence of APC, proliferated, did not become anergic, were smaller than control cells (data not shown), and suppressed proliferation of syngeneic naive CD4$^+$ T cells in vitro (FIG. 3A, right panel). In more detail, Naïve KJ1-26$^+$ CD4$^+$ tg T cells isolated from spleens of DO11.10 tg mice, were stained with CFSE and were activated with APC alone or APC+OVA. DO11.10 CD4$^+$ T cells activated for 3 weeks with APC+OVA (medium-cells) or APC+OVA+rapamycin (rapamycin-cells) were added in equal number to naïve CFSE$^+$ cells ($10^5:10^5$) (left panel). Alternatively, naive CD4$^+$ cells isolated from spleens of Balb/c mice were labeled with CFSE and cultured alone (unstimulated) or with αCD3 mAb. Balb/c CD4$^+$ T cells activated for 3 weeks with αCD3+αCD28 mAbs (medium-cells) or αCD3+αCD28 mAbs+rapamycin (rapamycin-cells) were added in equal number to naïve CFSE$^+$ cells ($10^5:10^5$) (right panel). After 5 days of culture, cell division was monitored by levels of CFSE dilution, Histograms show the FACs profile of CD4$^+$CFSE$^+$ T cells. Number of events in each cell division (n) are indicated on top of each peak. The amount of CD4$^+$CFSE$^+$ cells proliferating in the absence or presence of cultured T cells was calculated as described in the Methods and percentages of undivided cells in each culture condition is indicated. Percentages of suppression in comparison to proliferation of naïve control cells is indicated.

These data demonstrate that rapamycin induces Tr cells by directly acting on CD4$^+$ T cells.

The suppressive ability of rapamycin-exposed T cells was also tested in a transwell system in which responder and suppressor cells were kept separate. Using the same cells described in FIG. 3A (right panel), the experiment was performed in a transwell system in which responder naïve CD4$^+$ T cells were activated with αCD3 mAb at the bottom of the transwell while medium- or rapamycin-cells were pre-activated with αCD3 mAb for 6 hours and then added on top of the transwell (right panel). Data obtained in the transwell system were compared to data obtained in the co-colture system (left panel). Rapamycin-exposed T cells were able to suppress proliferation of syngeneic naïve CD4$^+$ T cells only in a co-culture system (FIG. 3A) indicating that their suppressive capacity was strictly dependent on cell-cell contact.

Figure 4A:
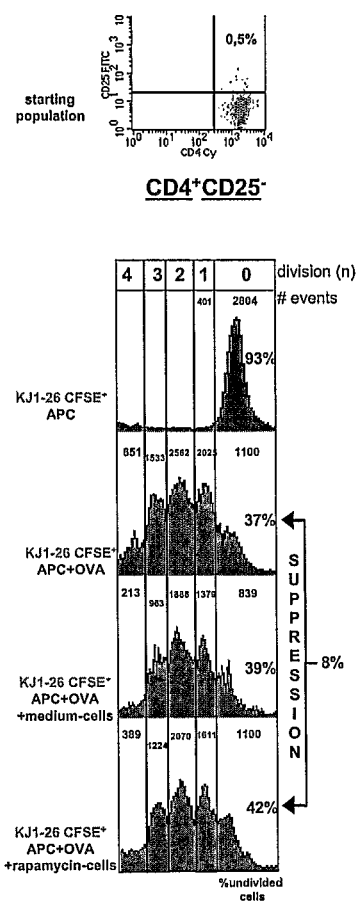
Figure 4B:
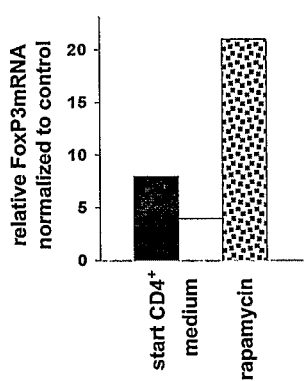
Figure 4B:
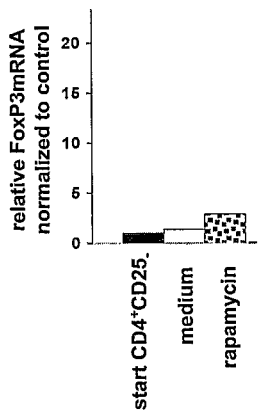

The presence of CD4$^+$CD25$^+$ Tr cells with suppressive activity in rapamycin-exposed T cell cultures may be due to either a de-novo induction of CD25$^+$ Tr cells from CD25$^-$ T cells or to a selective expansion of the naturally occurring CD4$^+$CD25$^+$FOXP3$^+$ Tr cell subset already present in limited amounts at the beginning of the culture (i.e. the ~10% of CD4$^+$CD25$^{bright}$ T cells usually found in a naive spleen). To address this question, CD4$^+$ T cells depleted of the CD25$^+$ Tr cells were cultured for three weeks in the presence or absence of rapamycin. In contrast to CD4$^+$ T cells (FIG. 3A), CD4$^+$CD25$^-$ T cells activated in the presence of rapamycin gave rise to a population of T cells that failed to suppress cell proliferation in vitro (FIG. 4A). Accordingly, FOXP3 expression was enhanced only in CD4$^+$ T cells exposed to rapamycin but not in CD4$^+$CD25$^-$ rapamycin-treated T cells (FIG. 4B). In more detail, the same experiment described in FIG. 3A (left panel) with cells from DO11.10 tg mice was performed using CD4$^+$CD25$^-$ T cells cultured for 3 weeks with APC+OVA (medium-cells) or APC+OVA+rapamycin (rapamycin-cells). The cultured cells were added in equal number to naïve KJ1-26$^+$CFSE$^+$ cells ($10^5$:$10^5$) and proliferation was monitored by CFSE dilution. FACS profile of the cells used before culture (starting population) is shown on top in FIG. 4A. Relative levels of mRNA FOXP3 were determined by real time quantitative RT-PCR in CD4$^+$ (left panel) or CD4$^+$CD25$^-$ (right panel) T cells repetitively activated in vitro with or without rapamycin. The amounts of FOXP3 mRNA are expressed as relative to that in splenocytes depleted of CD4$^+$CD25$^+$ T cells (which was given an arbitrary value of 1). Relative levels of mRNA FOXP3 in the cells before culture (start) are also indicated in FIG. 4B.

Figure 5A:
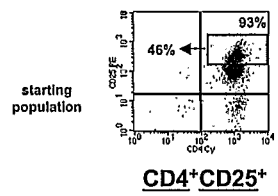

These data indicate that depletion of CD4$^+$CD25$^+$ T cells from the starting cell population does not allow the rapamycin-mediated expansion of Tr cells. However, one can not exclude the possibility that CD4$^+$CD25$^+$ Tr cells are indispensable in the culture for the generation of rapamycin-mediated induction of Tr cells from a CD4$^+$CD25$^-$ T cell population. To address this point, highly purified sorted CD4$^+$CD25$^+$ T cells (FIG. 5A) were activated with αCD3 and αCD28 mAbs and cultured for three weeks in the presence or absence of rapamycin. Thus, CD4$^+$CD25$^+$ T cells isolated from spleens of Balb/c mice were sorted by FACS and the FACS profile of sorted CD4$^+$CD25$^+$ T cells is shown in FIG. 5A. Sorted cells were 93% CD4$^+$CD25$^+$ among which 46% were CD4$^+$CD25$^{bright}$ T cells. High doses of IL-2 (i.e. 1000 U/ml) in the cultures were necessary to expand sorted CD4$^+$CD25$^+$ T cells, which otherwise were anergic (data not shown).

Figure 5B:
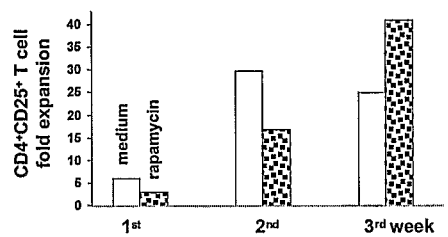
Figure 5C:
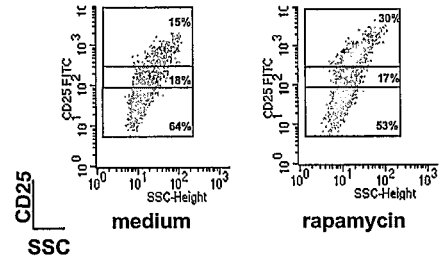

Fold expansion of Balb/c CD4$^+$CD25$^+$ T cells 1, 2, and 3 weeks after culture in the presence of αCD3+αCD28+1000 U/ml IL-2 (medium, white bars) or αCD3+αCD28+1000 U/ml IL-2+rapamycin (rapamycin, dotted bars) was evaluated by direct cell counts. After 3 rounds of stimulation with αCD3+αCD28+1000 U/ml IL-2 (medium) or αCD3+αCD28+1000 U/ml IL-2+rapamycin (rapamycin), Balb/c CD4$^+$CD25$^+$ T cells were left resting for one week with no further stimulation in the presence of low dose IL-2 (50 U/ml). After seven days, cells were analyzed by FACS. Cells were gated on CD4$^+$CD25$^+$ cells and numbers represent percentages of the three different CD25$^+$ subset (i.e. bright, dim, and low). The results are shown in FIGS. 5B and C. T cells activated in the presence of rapamycin had a delayed kinetic of proliferation compared to control cells. However, starting from the third week of culture, CD4$^+$CD25$^+$ T cells activated in the presence of rapamycin greatly expanded while control T cells showed reduced proliferation likely due to exaustion after repeated TCR stimulation in the presence of high doses of IL-2 (FIG. 5B). CD4$^+$CD25$^+$ T cells activated for three weeks in the presence of rapamycin contained a higher percentage of CD4$^+$CD25$^{bright}$ T cells compared to control cells (FIG. 5C).

The same experiment described in FIG. 3A (right panel) with cells from Balb/c mice was performed using CD4$^+$CD25$^+$ T cells cultured for 3 weeks with αCD3+αCD28+1000 U/ml IL-2 (medium-cells) or αCD3+αCD28+1000 U/ml IL-2+rapamycin (rapamycin-cells). The cultured cells were added in equal number to naïve CD4$^+$ T cells isolated from Balb/c mice ($10^5$:$10^5$) and proliferation was monitored by CFSE dilution.

Relative levels of mRNA FOXP3 were determined by real time quantitative RT-PCR in Balb/c CD4$^+$CD25$^+$ T cells repetitively activated in vitro with or without rapamycin. The amounts of FOXP3 mRNA are expressed as relative to that in splenocytes depleted of CD4$^+$CD25$^+$ T cells (which was given an arbitrary value of 1). Relative levels of mRNA FOXP3 in the cells before culture (start) are also indicated.

Figure 6A:
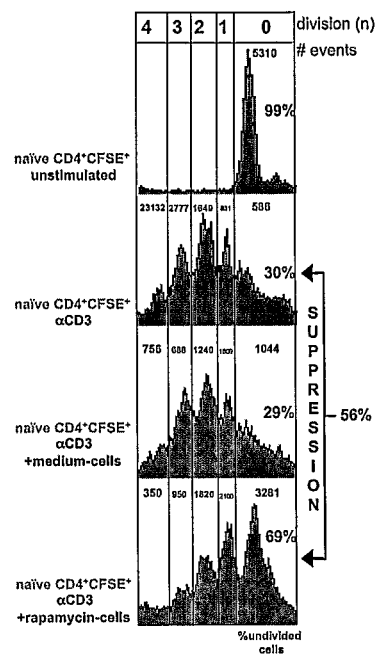
Figure 6B:
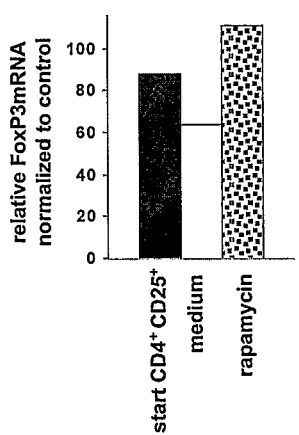

Accordingly, only rapamycin-exposed CD4$^+$CD25$^+$ T cells suppressed proliferation of syngeneic CD4$^+$ T cells in vitro (FIG. 6A) and preserved FOXP3 expression (FIG. 6B). Surprisingly, CD4$^+$CD25$^+$ T cells expanded in the absence of rapamycin lost their suppressive function in vitro (FIG. 6A). While it has been previously shown that CD4$^+$CD25$^+$ T cells can be expanded in vitro for 1 week with αCD3 and αCD28 mAbs and high doses of IL-2 without loosing their suppressive function (Taylor 2002), it is possible that repeated activation and culture of CD4$^+$CD25$^+$ T cells in medium and high doses of IL-2 results in an overgrowth of activated CD4$^+$CD25$^+$ effector T cells rather than an expansion of CD4$^+$CD25$^+$ Tr cells.

Figure 7:
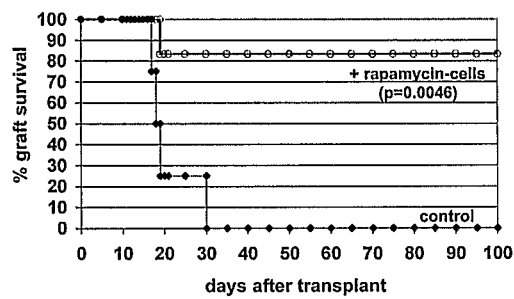

Diabetic Balb/c mice were transplanted under the kidney capsule with pancreatic β-islets purified from C57BL/6 mice. Mice were not treated (control n=4), or injected the day before the transplant with 5×$10^6$ CD4$^+$ T cells isolated from Balb/c mice and activated for 3 weeks in the presence of rapamycin (rapamycin-cells, n=6). Graft survival was monitored by glycemia levels. A graft was considered rejected when glycemia was higher than 250 mg/dl. Kaplan Meier survival curves were compared by the log-rank test. The results are shown in FIG. 7

Overall these data demonstrate that rapamycin selectively expands the naturally occurring CD4$^+$CD25+FOXP3$^+$ Tr cells normally present in the naïve splenic CD4$^+$ T cell compartment and that CD4$^+$CD25$^+$ Tr cells repetitively activated for three weeks in the presence of high doses of IL-2 preserve their phenotype and in vitro suppressive function only when cultured in the presence of rapamycin.

Materials and Methods for Example 3

Mice.

NOD female mice were purchased from Charles River Laboratories (Calco, Italy). All mice were kept under specific pathogen free conditions.

Murine T Cell Cultures.

CD4$^+$ T cells were obtained by incubation of splenocytes from pre-diabetic or diabetic NOD mice with αCD4 mAb-coated microbeads and applied onto MiniMacs columns (Miltenyi Biotec). The average purity was 95%. 1×$10^6$ CD4$^+$ T cells isolated from spleen of NOD mice were stimulated with coated 10 µg/ml of αCD3 and soluble 1 µg/ml of αCD28 mAbs (BD Biosciences). Cells were cultured in the presence of medium alone or 100 nM rapamycin (Sigma, St Louis, Mo.). Three rounds of stimulation of 7 days each were performed. IL-2 (BD Biosciences) was added starting from the second round of stimulation at 100 U/ml.

Suppression Experiments.

CD4$^+$ T cells isolated from pre-diabetic NOD mice were stained with CFSE (Molecular Probes) as described elsewhere (Lyons 1994) and cultured in 96 well plates ($2 \times 10^5$/well) coated with 10 µg/ml aCD3 mAb (BD Biosciences). T cells cultured for 3 weeks in medium or rapamycin were added in 1:1 ratio (i.e. $10^5$:$10^5$) to the culture, and 5 days later the cells were collected and analyzed by FACS. The percentage of CFSE$^+$ cells divided in the presence of cultured cells was compared to percentage of CFSE$^+$ divided cells in the absence of any added cells.

Example 3

Rapamycin Expands CD4$^+$CD25$^+$ Tr Cells from Normal and Diabetic NOD Mice

In this Example, we attempted to generate ex vivo Tr cells from non obese diabetic (NOD) mice. Spontaneously autoimmune diabetes in NOD mice mainly results from quantitative and qualitative changes in autoaggressive T effector cells. Older mice indeed harbor diabetogenic T cells that are progressively less prone to Tr cells-mediated inhibition (You et al. *Diabetes*, 2005). We tested whether rapamycin could expand functional Tr cells from NOD mice and whether these expanded T cells have a regulatory function. CD4$^+$ T cells were isolated from the spleen of pre-diabetic 11 week old NOD mice and were activated in vitro with anti-CD3 and CD28 mAbs in the presence of medium or rapamycin. After three round of stimulations, T cells cultured in the presence of rapamycin were highly enriched in CD4$^+$CD62L$^+$ and CD45RB$^{low}$ cells, and expressed higher levels of CD25 compared to medium culture conditions (data not shown). Interestingly, rapamycin-expanded NOD CD4$^+$ T cells not only were enriched in cells expressing regulatory markers, but were also suppressive in vitro (FIG. 8).

Figure 8:
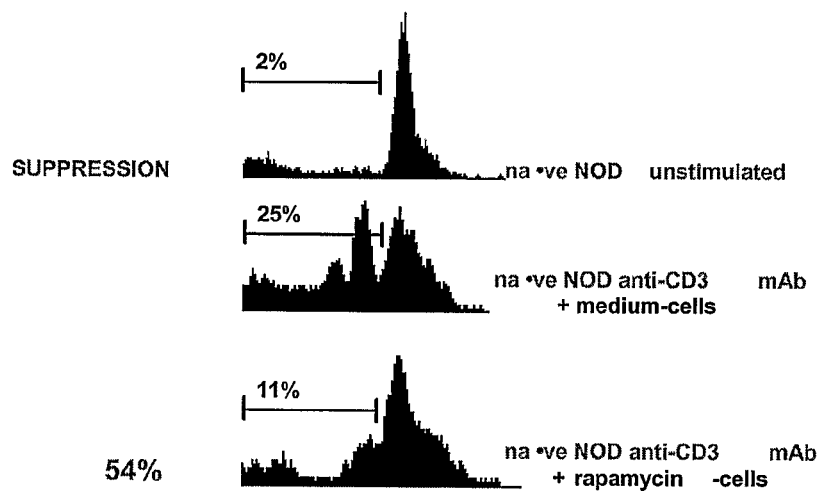
FIGS. 8-10 show the results of Example 3.

In more detail in relation to FIG. 8, T cells isolated from NOD mice and expanded ex vivo in the presence of rapamycin are suppressive in vitro. Naïve CD4$^+$ T cells isolated from spleens of pre-diabetic NOD mice were stained with CFSE and were cultured alone (unstimulated) or with anti-CD3 mAb. NOD CD4$^+$ T cells activated for 3 weeks in the presence of medium or rapamycin, and were added in equal number to naïve CFSE$^+$ cells ($10^5$:$10^5$). After 5 days of culture, cell division was monitored by levels of CFSE dilution. Histograms show the FACS profile of naïve CD4$^+$CFSE$^+$ T cells. Percentage of divided cells is shown on top of each histogram. Percentage of suppression in comparison to proliferation of naïve control cells in the presence of medium-cells is indicated on the left. One representative experiment out of 2 is presented.

Figure 9:
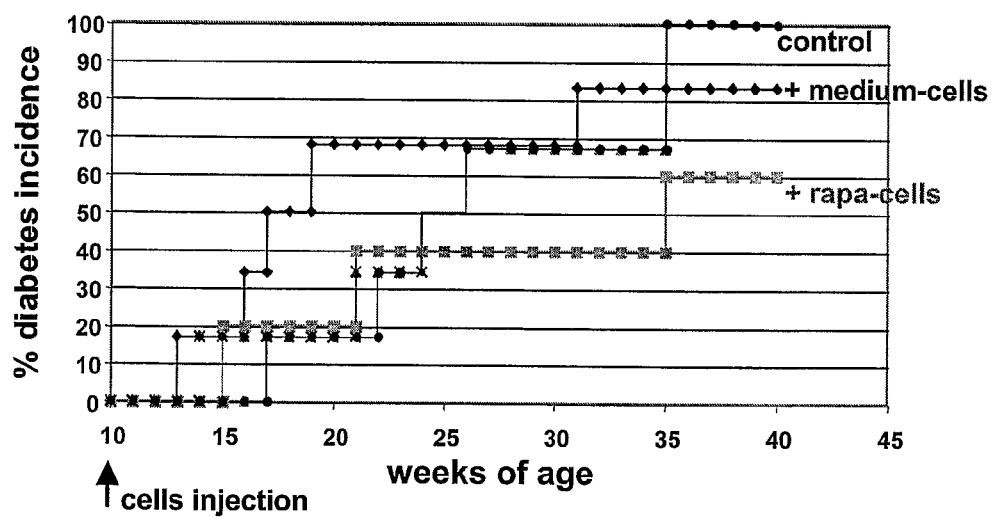

To test the ability of the ex vivo expanded NOD T cells to suppress autoimmune diabetes in vivo, 5 million of rapamycin-expanded T cells were injected in pre-diabetic NOD mice of 10 weeks of age and diabetes development was monitored throughout 30 weeks. At 40 weeks of age, all control non-injected NOD mice developed diabetes (n=6) and the adoptive transfer of medium-expanded T cells did not prevent diabetes. Interestingly, transfer of rapamycin-expanded T cells prevented diabetes development to some extent (60% diabetes incidence n=6) (FIG. 9). These preliminary data suggest that rapamycin can expand Tr cells ex vivo from pre-diabetic NOD mice which suppress cell proliferation in vitro and that these cells could prevent autoimmunity in vivo.

In more detail in relation to FIG. 9, Rapamycin-expanded NOD cells reduce diabetes development in vivo. Pre-diabetic NOD mice 10 week old were not treated (○ control n=6), or injected with $5 \times 10^6$ CD4$^+$ T cells isolated from NOD mice and cultured for 3 weeks with medium (♦ n=6) or rapamycin (■ n=5). Diabetes incidence was monitored by glycemia levels up to 40 weeks of age.

Figure 10:
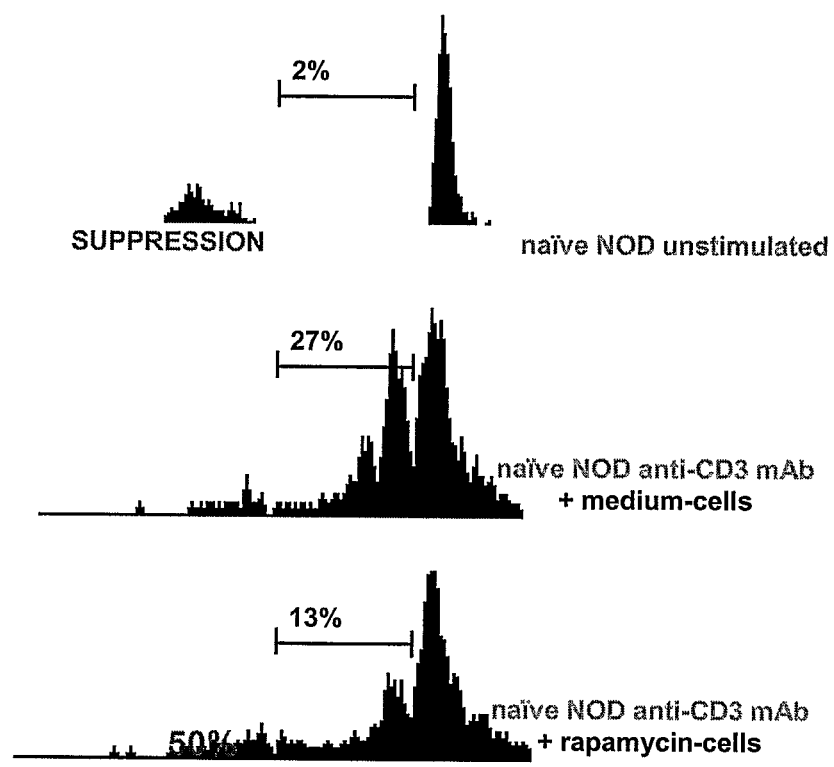

A cellular-therapy-based approach to treat type 1 diabetes is likely to require the use of autologous T cells isolated from diabetic subjects. It is therefore crucial to define whether Tr cells can be expanded ex vivo from already diabetic individuals. To this attempt, we defined whether rapamycin can expand ex vivo Tr cells from overtly diabetic NOD mice. CD4$^+$ T cells were isolated from the spleen of NOD mice with overt diabetes and were expanded ex vivo for 3 weeks with anti-CD3 and CD28 mAbs in the presence or absence of rapamycin. At the end of the third week of stimulation, the expanded T cells were tested for their ability to suppress syngeneic CD4$^+$ T cells in vitro. T cells expanded with rapamycin efficiently suppressed cell proliferation (FIG. 10). These data indicate that rapamycin can efficiently expands Tr cells ex vivo also from a cell pool, which includes diabetogenic T cells.

In more detail in relation to FIG. 10, T cells isolated from diabetic NOD mice and expanded in the presence of rapamycin are suppressive in vitro. Naïve CD4$^+$ T cells isolated from spleens of pre-diabetic NOD mice were stained with CFSE and were cultured alone (unstimulated) or with anti-CD3 mAb. CD4$^+$ T cells isolated from diabetic NOD and activated for 3 weeks in the presence of medium, or rapamycin, were added in equal number to naïve CFSE$^+$cells ($10^5$:$10^5$). After 5 days of culture, cell division was monitored by levels of CFSE dilution. Histograms show the FACS profile of CD4$^+$ CFSE$^+$ T cells. Percentage of divided cells is shown on top of each histogram. Percentage of suppression in comparison to proliferation of naïve control cells in the presence of medium-cells is indicated on the left.

Overall these new data demonstrate that rapamycin selectively expands the naturally occurring CD4$^+$CD25$^+$FOXP3$^+$ Tr cells present in the spleen of normal and diabetic NOD mice.

Materials and Methods for Examples 4-8

Cell Purification.

Peripheral blood mononuclear cells were separated by density-gradient centrifugation over Lymphoprep (Amersham Biosciences). CD4$^+$ T cells were purified by negative selection using a CD4$^+$ T cell enrichment kit (Miltenyi Biotec, Bergisch Gladbach, Germany).

Flow Cytometry.

Cells were stained with the indicated surface Abs (all from BD Biosciences, Mountain View, Calif.), and were analyzed with a FACScan flow cytometer equipped with CellQuest software (BD Biosciences). Intra-cytoplasmic staining for h-FOXP3 was performed using the anti-FOXP3 APC staining Kit (eBioscience) following the product instruction.

T Cell Cultures.

CD4$^+$ T cells isolated from PBMCs of healthy subjects or T1D patients were activated with plate bound anti-CD3 (10 µg/ml) and soluble of anti-CD28 (1 µg/ml) mAbs (BD Biosciences). Cells were cultured in the presence of medium (x-vivo 10) alone or with 100 nM rapamycin (Sigma, St Louis, Mo.). Three round of stimulations of 7 days each were performed. IL-2 (BD Biosciences) was added starting from the second round of stimulation at 100 U/ml.

Suppression Experiments.

Purified CD4$^+$ T cells or CD4$^-$ PBMCs from healthy subjects or T1D patients were stained with CFSE (Molecular Probes, Eugene, Oreg.) as described elsewhere {Lyons, 1994 #22} and cultured in 96 well plates (2×10$^5$/well) pre-coated with anti-CD3 (10 μg/ml) and with soluble of anti-CD28 (1 μg/ml) mAbs (BD Biosciences). T cells cultured for 3 weeks in medium or rapamycin were first stained with SNARF (Molecular Probes) following the same protocol as for CFSE staining, and subsequently were added in 1:1 ratio (i.e. 10$^5$: 10$^5$) to the culture. Seven days later the cells were collected and analyzed by FACS. The percentage of CFSE$^+$ cells divided in the presence of cultured cells was compared to percentage of CFSE$^+$ divided cells in the absence of any added cells.

The proportion of CFSE$^+$ (FL-1) responding T cells proliferating in vitro was calculated by gating on lymphocytes and alive cells (TOPRO$^-$ FL-4, Molecular Probe) and by excluding SNARF$^+$ (FL-2) cells. The number of gated cells (events) in a given cycle (division: n) was divided by 2 raised to power n, to calculate the percentage of original precursor cells from which they arose. The sum of original precursors from division 1 to 6 represents the number of precursors cells which proliferated. The percent of CFSE$^+$ divided cells was calculated by [(# of precursors that proliferated$_{1-6}$/# of total precursors$_{0-6}$)×100] {Lyons, 1994 #22}.

Example 4

Rapamycin Strongly Reduces TCR-Mediated Proliferation of CD4$^+$ T Cells and Does Not Induce T Cell Anergy CD4$^+$ T cells were stained with CFSE either at the beginning of the culture (1$^{st}$ week), or at the end of one (2$^{nd}$ week), or three (4$^{th}$ week) round of stimulations. CFSE$^+$ CD4$^+$ T cells were activated in vitro in the presence of anti-CD3+anti-CD28 mAbs in the presence or absence of 100 nM rapamycin. CFSE dilution was monitored 7 days after activation. One representative experiment out of 6 is presented in FIG. 11A.

Figure 11:
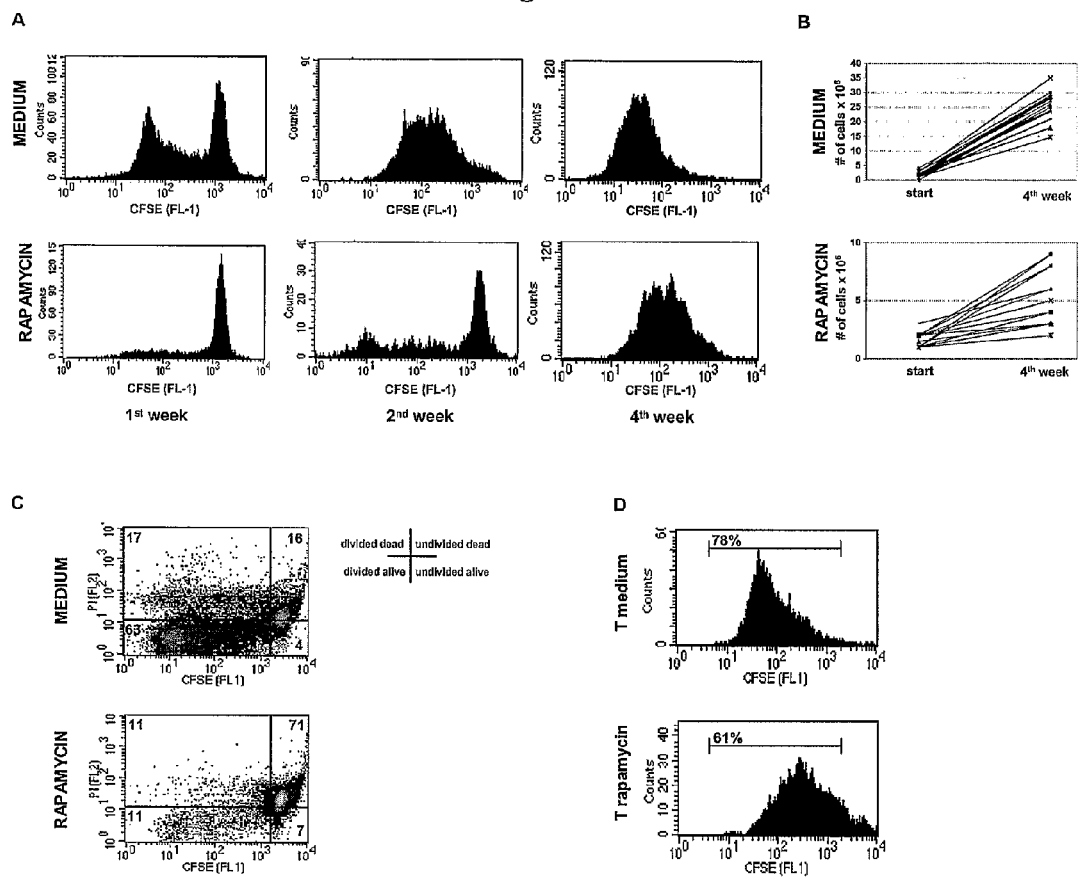
FIG. 11 shows the results of Example 4.

In FIG. 11B the number of CD4$^+$ T cells present at the beginning (start) and at the end (4$^{th}$ week) of the culture in the presence or absence of rapamycin is shown. Each line represents one experiment (n=14).

CD4$^+$ T cells were stained with CFSE and activated with anti-CD3+anti-CD28 mAbs in the presence or absence of rapamycin. After seven days, cells were stained with propidium iodide (PI) and were analyzed by FACS. Numbers represent percentages of divided dead cells (CFSE$^{diluted}$-PI$^+$), undivided dead cells (CFSE$^{undiluted}$-PI$^+$), undivided alive cells (CFSE$^{undiluted}$-PI$^-$), and divided alive cells (CFSE$^{diluted}$-PI$^-$). In FIG. 11C one representative experiment out of 5 is presented.

After 3 round of stimulations with anti-CD3+anti-CD28 mAbs (T medium) or anti-CD3+anti-CD28 mAbs+rapamycin (T rapamycin), CD4$^+$ T cells were stained with CFSE and re-stimulated with anti-CD3+anti-CD28 mAbs in the absence of the compound and of exogenous IL-2. CFSE dilution was monitored 7 days after activation. Numbers indicate the percentage of dividing cells. One representative experiment out of 3 is presented in FIG. 11D.

Example 5

Rapamycin-Expanded CD4$^+$ T Cells Express Regulatory Markers and Suppress Proliferation of Syngeneic and Allogeneic CD4$^+$ and CD8$^+$ T Cells Expression of CD25 and FOXP3 by freshly isolated CD4$^+$ T cells before culture was tested by FACS. The results are shown in FIG. 12A.

After 3 rounds of stimulation with anti-CD3+anti-CD28 mAbs (T medium) or or anti-CD3+anti-CD28 mAbs+rapamycin (T rapamycin), CD4$^+$ T cells were left resting for one week with no further stimulation in the presence of IL-2 (10 U/ml). After seven days cells were analyzed by FACS. One representative experiment out of 8 is presented in FIG. 12B.

Figure 12:
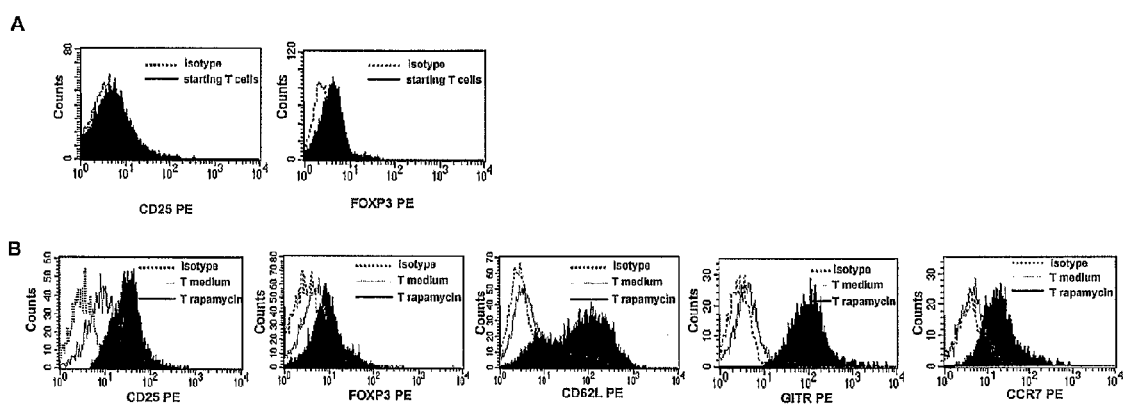
FIG. 12 shows the results of Example 5.
Figure 12:
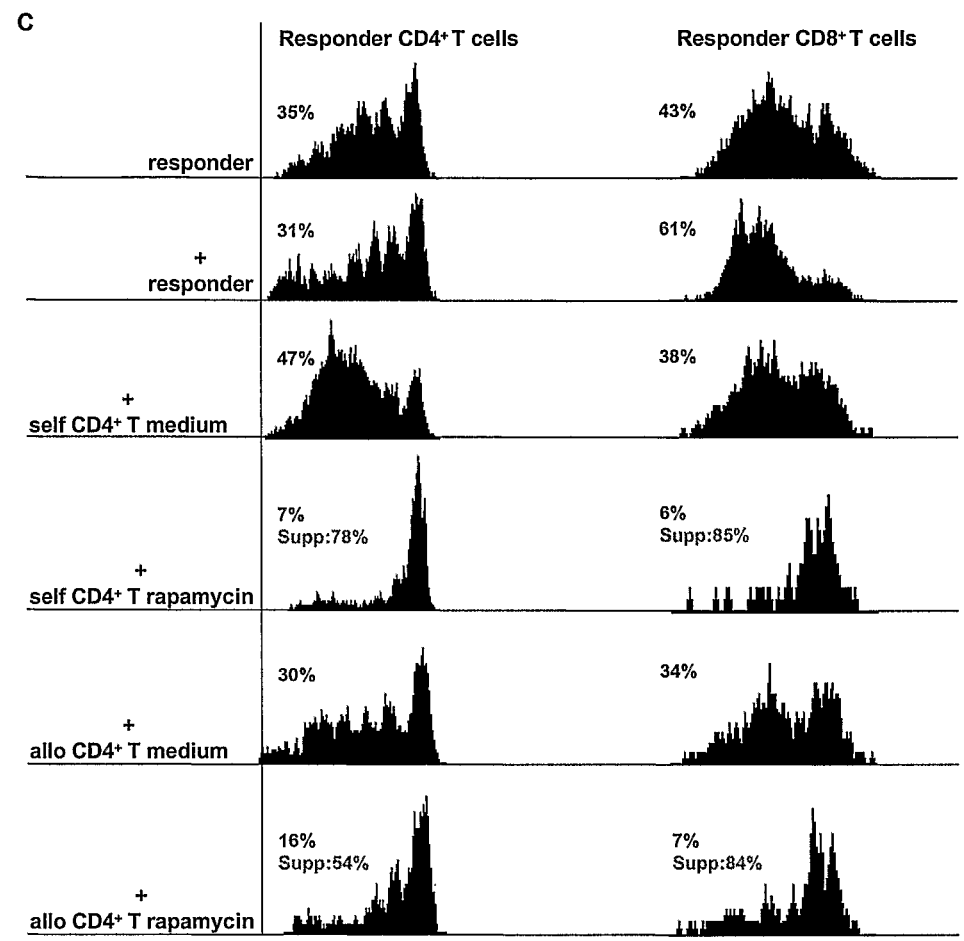
Figure 12:
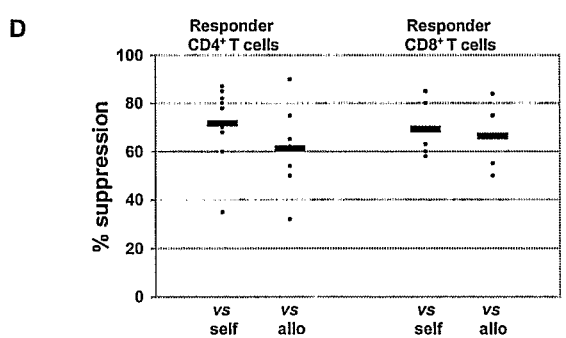

Purified CD4$^+$ T cells isolated from healthy subject, were stained with CFSE and were activated with anti-CD3+anti-CD28 mAbs (responder CD4$^+$ T cells, FIG. 12C left panel). Alternatively, CD4$^-$ cells isolated from healthy subject, were stained with CFSE and were activated with anti-CD3+anti-CD28 mAbs. Proliferation of CD8$^+$ T cells was followed upon staining with anti-CD8 mAb at the moment of FACS analysis (responder CD8$^+$ T cells, FIG. 12C right panel). CD4$^+$ T cells isolated from the same subject used as responder (self) or from an unrelated donor (allo) and activated for 3 weeks with anti-CD3+anti-CD28 mAbs (T medium) or anti-CD3+anti-CD28 mAbs+rapamycin (T rapamycin) were added in equal number to responder CFSE$^+$ cells (10$^5$:10$^5$). After 7 days of culture, cell division was monitored by levels of CFSE dilution. Histograms show the FACS profile of CFSE$^+$ T cells. The amount of CFSE$^+$ cells proliferating in the absence or presence of cultured T cells was calculated and percentages of divided cells in each culture condition is indicated. Percentages of suppression in comparison to proliferation of responder cells is indicated. One representative experiment is presented in FIG. 12C.

Percentage of suppression in each performed experiments is presented in FIG. 12D. Each dot represents one experiment. The line represents average of suppression. There was no statistically significant differences between suppression versus responder self-CD4$^+$ T cells and versus allo-CD4$^+$ T cells.

Example 6

Figure 13:
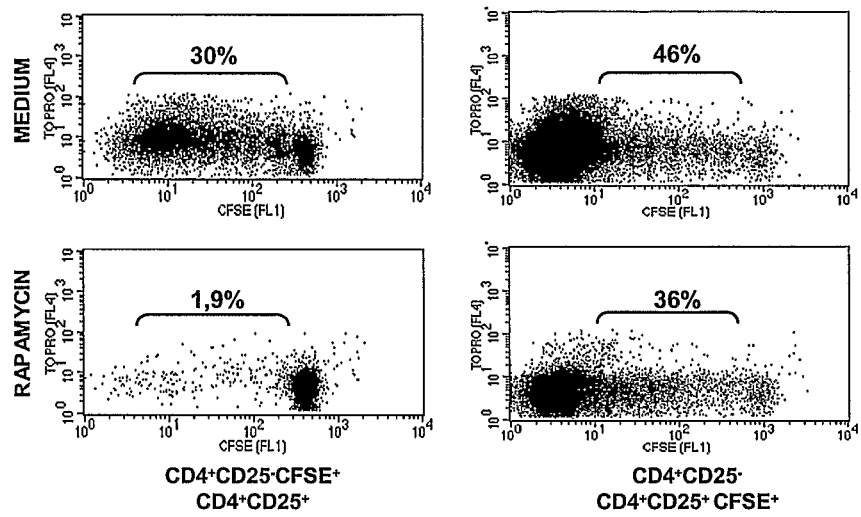
FIG. 13 shows the results of Example 6.

Rapamycin Selectively Blocks TCR-Mediated Proliferation of CD4$^+$CD25$^-$ T Cells but not of CD4$^+$CD25$^+$ Tr Cells CD4$^+$CD25$^-$ and CD4$^+$CD25$^{bright}$ T cells were FACS sorted. Subsequently, sorted CD4$^+$CD25$^-$ T cells were stained with CSFE and sorted CD4$^+$CD25$^+$ T cells were added back to the same amount present in unsorted CD4$^+$ T cells (5%) (FIG. 13, left panel). Alternatively, sorted CD4$^+$CD25$^+$ T cells were stained with CSFE and sorted CD4$^+$CD25$^-$ T cells were added back to the same amount present in unsorted CD4$^+$ T cells (95%) (right panel of FIG. 13). The two distinct CFSE stained cell populations were activated with anti-CD3+anti-CD28 mAbs+IL-2 in the presence or absence of 100 nM rapamycin. CFSE dilution was monitored 7 days after activation. Numbers indicate the percentage of CFSE$^+$ dividing cells. One representative experiment out of 2 is presented in FIG. 13.

Example 7

CD4$^+$ T Cells of Normal Donors and T1D Patients Express Similar Levels of FOXP3

Figure 14:
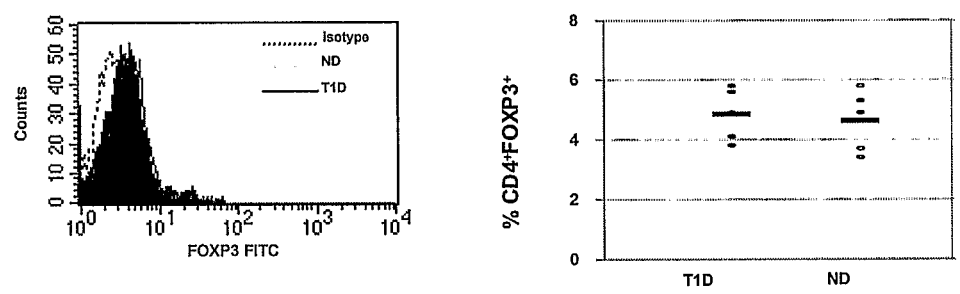
FIG. 14 shows the results of Example 7.

FOXP3 expression was tested by FACS on purified CD4$^+$ T cells isolated from normal donors (ND) and type 1 diabetic patients (T1D). One representative histogram is shown in FIG. 14. Percentage of CD4+FOXP3+ cells in each T1D patients tested (n=5) and in ND is also shown. Each dot represents one donor. The line represents average of CD4+ FOXP3+ T cells. There was no statistically significant differences between FOXP3-expressing cells in ND versus T1D subjects. No difference in FOXP3 expression between ND and T1D patients was observed when the analysis was performed on CD4+CD25$^{bright}$ T cells.

Example 8

Figure 15:
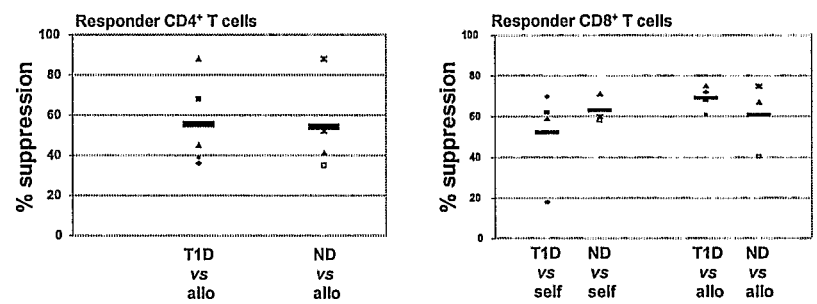
FIG. 15 shows the results of Example 8.

Rapamycin-Expanded CD4+ T Cells from T1D Patients Suppress Proliferation of CD4+ and CD8+ T Cells CD4+ T cells isolated from normal donor, were stained with CFSE and were activated with anti-CD3+anti-CD28 mAbs (responder CD4+ T cells, FIG. 15 left panel). Alternatively, CD4− cells isolated from T1 D patient (middle panel) or normal donor (right panel), were stained with CFSE and were activated with anti-CD3+anti-CD28 mAbs. Proliferation of CD8+ T cells was followed upon staining with anti-CD8 mAb at the moment of FACS analysis (responder CD8+ T cells). CD4+ T cells isolated from the same subject used as responder (self) or from an unrelated donor (allo) and activated for 3 weeks with anti-CD3+anti-CD28 mAbs (T medium) or anti-CD3+anti-CD28 mAbs+rapamycin (T rapamycin) were added in equal number to responder CFSE+ cells (10$^5$:10$^5$). After 7 days of culture, cell division was monitored by levels of CFSE dilution. Histograms in FIG. 15 show the FACS profile of CFSE+ T cells. The amount of CFSE+ cells proliferating in the absence or presence of cultured T cells was calculated as described in the above methods and percentages of divided cells in each culture condition is indicated. Percentages of suppression in comparison to proliferation of responder cells is indicated.

Percentage of suppression in each performed experiments is presented. Each dot represents one experiment. The line represents average of suppression.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in cellular and/or molecular biology or related fields are intended to be within the scope of the following claims.

REFERENCES

Abraham R T, Wiederrecht G J. Immunopharmacology of rapamycin. Annu Rev Immunol. 1996; 14:483-510

Battaglia M, Blazar B R, Roncarolo M G. The puzzling world of murine T regulatory cells. Microbes Infection 2002; 4: 559-566.

Belghith M, Bluestone J A, Barriot S, Megret J, Bach J F, Chatenoud L. TGF-beta-dependent mechanisms mediate restoration of self-tolerance induced by antibodies to CD3 in overt autoimmune diabetes. Nat Med. 2003; 9:1202-1208

Blaha P, Bigenzahn S, Koporc Z, Schmid M, Langer F, Selzer E, Bergmeister H, Wrba F, Kurtz J, Kiss C, Roth E, Muehlbacher F, Sykes M, Wekerle T. The influence of immunosuppressive drugs on tolerance induction through bone marrow transplantation with costimulation blockade. Blood. 2003; 101:2886-2893

Chung J, Kuo C J, Crabtree G R, Blenis J. Rapamycin-FKBP specifically blocks growth-dependent activation of and signaling by the 70 kd S6 protein kinases. Cell. 1992; 69:1227-1236

Davalli A M, Scaglia L, Zangen D H, Hollister J, Bonner-Weir S, Weir G C. Vulnerability of islets in the immediate posttransplantation period. Dynamic changes in structure and function. Diabetes. 1996; 45:1161-1167

Dumont F J, Staruch M J, Koprak S L, Melino M R, Sigal N H. Distinct mechanisms of suppression of murine T cell activation by the related macrolides FK-506 and rapamycin. J Immunol. 1990; 144:251-258

Edinger M, Hoffmann P, Ermann J, Drago K, Fathman C G, Strober S, Negrin R S. CD4+CD25+ regulatory T cells preserve graft-versus-tumor activity while inhibiting graft-versus-host disease after bone marrow transplantation. Nat Med. 2003 9:1144-50.

Fehervari Z, Sakaguchi S. Development and function of CD25+CD4+regulatory T cells. Curr Opin Immunol. 2004; 16:203-208

Fingar D C, Salama S, Tsou C, Harlow E, Blenis J. Mammalian cell size is controlled by mTOR and its downstream targets S6K1 and 4EBP1/eIF4E. Genes Dev. 2002; 16:1472-1487

Ghobrial R, Karczewski M, Ferraresso M, Tian L, Stepkowski S M, Kahan B D. Kinetics of in vitro immune responses of T and B cells during tolerance induction by sirolimus. Ann Transplant. 1996; 1:22-29

Hackstein H, Taner T, Logar A J, Thomson A W. Rapamycin inhibits macropinocytosis and mannose receptor-mediated endocytosis by bone marrow-derived dendritic cells. Blood. 2002; 100:1084-1087

Hojo, M., T. Morimoto, et al. Cyclosporine induces cancer progression by a cell-autonomous mechanism. Nature 1999; 397: 530-5344.

Kahan B D, Camardo J S. Rapamycin: clinical results and future opportunities. Transplantation. 2001; 72:1181-1193

Kato J Y, Matsuoka M, Polyak K, Massague J, Sherr C J. Cyclic AMP-induced G1 phase arrest mediated by an inhibitor (p27Kip1) of cyclin-dependent kinase 4 activation. Cell. 1994; 79:487-496

Koenen H J, Michielsen E C, Verstappen J, Fasse E, Joosten I. Superior T-cell suppression by rapamycin and FK506 over rapamycin and cyclosporine A because of abrogated cytotoxic T-lymphocyte induction, impaired memory responses, and persistent apoptosis. Transplantation. 2003; 75:1581-1590

Levings M K, Sangregorio R, Sartirana C, Moschin A L, Battaglia M, Orban P C, Roncarolo M G. Human CD25+ CD4+ T suppressor cell clones produce transforming growth factor beta, but not interleukin 10, and are distinct from type 1 T regulatory cells. J Exp Med. 2002; 196:1335-1346

Lyons A B, Parish C R. Determination of lymphocyte division by flow cytometry. J Immunol Methods. 1994; 171:131-137

Morice W G, Brunn G J, Wiederrecht G, Siekierka J J, Abraham R T. Rapamycin-induced inhibition of p34cdc2 kinase activation is associated with G1/S-phase growth arrest in T lymphocytes. J Biol Chem. 1993; 268:3734-3738

Nourse J, Firpo E, Flanagan W M, Coats S, Polyak K, Lee M H, Massague J, Crabtree G R, Roberts J M. Interleukin-2-mediated elimination of the p27Kip1 cyclin-dependent kinase inhibitor prevented by rapamycin. Nature. 1994; 372:570-573

Powell J D, Lerner C G, Schwartz R H. Inhibition of cell cycle progression by rapamycin induces T cell clonal anergy even in the presence of costimulation. J Immunol. 1999; 162:2775-2784

Saunders R N, Metcalfe M S, Nicholson M L. Rapamycin in transplantation: a review of the evidence. Kidney Int. 2001; 59:3-16

Schmelzle T, Hall M N. TOR, a central controller of cell growth. Cell. 2000; 103:253-262

Sehgal S N. Rapamune (RAPA, Rapamycin, sirolimus): mechanism of action immunosuppressive effect results from blockade of signal transduction and inhibition of cell cycle progression. 1998 Clin Biochem 31: 335-40.

Taams L, Vukmanovic-Stejic M, Salmon M, Akbar A. Immune regulation by CD4+CD25+ regulatory T cells: implications for transplantation tolerance. Transpl Immunol. 2003; 11:277-285

Taylor P A, Lees C J, Blazar B R. The infusion of ex vivo activated and expanded CD4(+)CD25(+) immune regulatory cells inhibits graft-versus-host disease lethality. Blood. 2002; 99:3493-3499

Terada N, Franklin R A, Lucas J J, Blenis J, Gelfand E W. Failure of rapamycin to block proliferation once resting cells have entered the cell cycle despite inactivation of p70 S6 kinase. J Biol Chem. 1993; 268:12062-12068

Terada N, Takase K, Papst P, Nairn A C, Gelfand E W. Rapamycin inhibits ribosomal protein synthesis and induces G1 prolongation in mitogen-activated T lymphocytes. J Immunol. 1995; 155:3418-3426

Trenado A, Charlotte F, Fisson S, Yagello M, Klatzmann D, Salomon B L, Cohen J L. Recipient-type specific CD4+ CD25+ regulatory T cells favor immune reconstitution and control graft-versus-host disease while maintaining graft-versus-leukemia. J Clin Invest. 2003 112:1688-96.

Wells A D, Li X C, Li Y, Walsh M C, Zheng X X, Wu Z, Nunez G, Tang A, Sayegh M, Hancock W W, Strom T B, Turka L A. Requirement for T-cell apoptosis in the induction of peripheral transplantation tolerance. Nat Med. 1999; 5:1303-1307

Vu M D, Amanullah F, Li Y, Demirci G, Sayegh M H, Li X C. Different costimulatory and growth factor requirements for CD4+ and CD8+ T cell-mediated rejection. J Immunol. 2004; 173:214-221

The invention claimed is:

1. A method of cellular therapy for the inhibitory or therapeutic treatment of type I diabetes mellitus, allogeneic solid organ rejection or graft versus host disease, or the therapeutic treatment of other autoimmune diseases, comprising the steps of:
   (a) incubating $CD4^+$ T cells obtained from a human or animal with:
      (i) a cytokine,
      (ii) a compound selected from the group consisting of rapamycin, rapamycin 42-ester with 3-hydroxy-2-(hydroxymethyl)-2-methylpropionic acid, and 42-0-(2-hydroxy)ethyl rapamycin, and
      (iii) anti-CD3 and anti-CD28 antibodies or an antigen in the presence of antigen presenting cells;
   (b) isolating the resultant population of $CD4^+CD25^+$ T regulatory (Tr) cells; and
   (c) introducing into a patient the $CD4^+CD25^+$ Tr cells;
   wherein the only cytokine used to incubate the $CD4^+$ T cells prior to the isolating step (b) consists of IL-2.

2. The method according to claim 1, wherein the $CD4^+CD25^+$ Tr cells are introduced into the patient in combination with a drug.

3. The method according to claim 1 wherein the $CD4^+$ T cells obtained from a human or animal are purified prior to the incubating step.

4. The method according to claim 3, wherein: (a)(iii) is an antigen in the presence of antigen presenting cells; and the antigen is selected from the group consisting of an allergen, an allo-antigen, a self-antigen, a food antigen, and a microbial antigen.

5. The method according to claim 1, wherein the $CD4^+CD25^+$ Tr cells are introduced into the patient as a composition comprising the $CD4^+CD25^+$ Tr cells and a pharmaceutically acceptable carrier, excipient, or diluent.

6. The method according to claim 1, wherein the $CD4^+CD25^+$ Tr cells are introduced in an amount effective to inhibit allogeneic solid organ rejection or graft versus host disease.

7. The method according to claim 1, wherein the patient suffers from a disease or disorder selected from the group consisting of: autoimmune (Hasimoto's) thyroiditis, hyperthyroidism (Graves' disease) type I diabetes mellitus, insulin resistant diabetes, autoimmune adrenal insufficiency (addison's disease), autoimmune oophoirits, autoimmune orchitis, autoimmune hemolytic anemia, paroxysmal cold hemoglobinuria, autoimmune thrombocytopenia, autoimmune neutropenia, pernicius anemia, pure red cell anemia, autoimmune coagulopathies, myasthenia gravis, autoimmune polyneuritis, multiple sclerosis, experimental allergic encephalomyelitis, pemphigus and other bullous diseases, rheumatic carditis, Goodpasture's syndrome, postcardiotomy syndrome, systemic lupus erythematosus, rheumatoid arthritis, Sjorgen's syndrome, polymyositis, dermatomyositis, scleroderma; inflammatory bowel diseases: Chron's disease, ulcerative colitis; chronic obstructive pulmonary diseases; chronic inflammatory diseases; allergic diseases: asthma, atopic dermatitis; fibrotic diseases; and immune reactions to gene therapy derived products.

8. The method according to claim 1, wherein the compound in the incubating step is rapamycin.

9. The method according to claim 1 comprising: obtaining a sample comprising T cells from a human or animal; and isolating T cells that are $CD4^+$ and $CD25^+$ prior to the incubating step.

10. The method according to claim 1, further comprising a step of purifying $CD25^+$ T cells prior to or subsequent to the incubating of the T cells with rapamycin, rapamycin 42-ester with 3-hydroxy-2-(hydroxymethyl)-2-methylpropionic acid, or 42-0-(2-hydroxy)ethyl rapamycin.

11. The method according to claim 1, wherein the $CD4^+$ T cells comprise $CD4^+CD25^+$ Tr cells.

12. The method according to claim 11 wherein the $CD4^+$ T cells also comprise $CD4^+CD25^-$ T cells.

13. A method of cellular therapy for the inhibitory or therapeutic treatment of type I diabetes mellitus, allogeneic solid organ rejection or graft versus host disease, or the therapeutic treatment of other autoimmune diseases, comprising:
   (a) an incubation step consisting of incubating $CD4^+$ T cells obtained from a human or animal with:
      (i) a cytokine consisting of IL-2,
      (ii) a compound selected from the group consisting of rapamycin, rapamycin 42-ester with 3-hydroxy-2-(hydroxymethyl)-2-methylpropionic acid and 42-0-(2-hydroxy)ethyl rapamycin, and (iii) anti-CD3 and anti-CD28 antibodies or an antigen in the presence of antigen presenting cells;

(b) isolating a resultant population of CD4$^+$CD25$^+$ regulatory (Tr) cells after (a); and (c) introducing into a patient the CD4$^+$CD25$^+$ Tr cells after (b).

14. The method according to claim 13, wherein the resultant population of cells is introduced into the patient in combination with a drug.

15. The method according to claim 13, wherein the method comprises obtaining a sample comprising T cells from a human or animal.

16. The method according to claim 15, wherein the patient suffers from a disease or disorder selected from the group consisting of: autoimmune (Hasimoto's) thyroiditis, hyperthyroidism (Graves' disease) type I diabetes mellitus, insulin resistant diabetes, autoimmune adrenal insufficiency (addison's disease), autoimmune oophoirits, autoimmune orchitis, autoimmune hemolytic anemia, paroxysmal cold hemoglobinuria, autoimmune thrombocytopenia, autoimmune neutropenia, pernicius anemia, pure red cell anemia, autoimmune coagulopathies, myasthenia gravis, autoimmune polyneuritis, multiple sclerosis, experimental allergic encephalomyelitis, pemphigus and other bullous diseases, rheumatic carditis, Goodpasture's syndrome, postcardiotomy syndrome, systemic lupus erythematosus, rheumatoid arthritis, Sjorgen's syndrome, polymyositis, dermatomyositis, scleroderma; inflammatory bowel diseases: Chron's disease, ulcerative colitis; chronic obstructive pulmonary diseases; chronic inflammatory diseases; allergic diseases: asthma, atopic dermatitis; fibrotic diseases; and immune reactions to gene therapy derived products.

17. The method according to claim 15, wherein the sample comprising T cells is a blood sample or a sample from a lymphoid organ.

18. The method according to claim 15 or 17 wherein the T cells are purified prior to incubation with rapamycin.

19. The method according to claim 18, wherein (a)(iii) is an antigen in the presence of antigen presenting cells.

20. The method according to claim 19, where the antigen is selected from the group consisting of an allergen, an alloantigen, a self-antigen, a food antigen, and a microbial antigen.

21. A method of cellular therapy for the inhibitory or therapeutic treatment of type I diabetes mellitus, allogeneic solid organ rejection or graft versus host disease, or therapeutic treatment of other autoimmune diseases, comprising (a) obtaining a sample of CD4$^+$ T cells from a human or animal, optionally isolating CD4$^+$ T cells from the sample, and (b) an incubation step consisting of incubating CD4$^+$ T cells obtained from a human or animal with:

(i) a cytokine consisting of IL-2, (ii) a compound selected from the group consisting of rapamycin, rapamycin 42-ester with 3-hydroxy-2-(hydroxymethyl)-2-methylpropionic acid and 42-0-(2-hydroxy)ethyl rapamycin, and (iii) anti-CD3 and anti-CD28 antibodies or antigen in the presence of antigen presenting cells;

(c) isolating a resultant population of CD4$^+$CD25$^+$ T regulatory (Tr) cells after (b); and (d) introducing into a patient the CD4$^+$CD25$^+$ Tr cells after (c).

22. The method according to claim 21, further comprising a step of purifying CD25$^+$ T cells prior to or subsequent to incubating the T cells with rapamycin, rapamycin 42-ester with 3-hydroxy-2-(hydroxymethyl)-2-methylpropionic acid or 42-0-(2-hydroxy)ethyl rapamycin.

23. The method according to claim 15 or 21, wherein the T cells are introduced into the patient as a composition comprising the T cells and a pharmaceutically acceptable carrier, excipient, or diluent.

24. The method according to claim 15 or 21, wherein the T cells are introduced in an amount effective to inhibit allogeneic solid organ rejection or graft versus host disease.

25. The method according to claim 13 or 21 wherein the compound in the incubating step is rapamycin.

26. The method according to claim 15 or 21 comprising a step of isolating T cells that are CD4$^+$ and CD25$^+$ prior to the incubating step.

27. The method according to claim 26, comprising contacting T cells with an anti-CD25 antibody to isolate the T cells that are CD25$^+$.

28. A method of cellular therapy for the inhibitory or therapeutic treatment of type I diabetes mellitus, allogeneic solid organ rejection or graft versus host disease, or therapeutic treatment of other autoimmune diseases, comprising:

(a) purifying CD4$^+$ T cells obtained from a human or animal;

(b) an incubation step consisting of incubating CD4$^+$ T cells obtained from a human or animal with:

(i) a cytokine consisting of IL-2, (ii) a compound selected from the group consisting of rapamycin, rapamycin 42-ester with 3-hydroxy-2-(hydroxymethyl)-2-methylpropionic acid and 42-0-(2-hydroxy)ethyl rapamycin, and (iii) anti-CD3 and anti-CD28 antibodies or antigen in the presence of antigen presenting cells;

(c) isolating a resultant population of CD4$^+$CD25$^+$ T regulatory (Tr) cells after (b); and (d) introducing into a patient the CD4$^+$CD25$^+$ Tr cells after (c).

29. The method according to any of claim 13, 21, 22 or 28 wherein the autoimmune disease is selected from the group consisting of autoimmune (Hasimoto's) thyroiditis, hyperthyroidism (Graves' disease), insulin resistant diabetes, autoimmune adrenal insufficiency (Addison's disease), autoimmune oophoirits, autoimmune orchitis, autoimmune hemolytic anemia, paroxysmal cold hemoglobinuria, autoimmune thrombocytopenia, autoimmune neutropenia, pernicius anemia, pure red cell anemia, autoimmune coagulopathies, myasthenia gravis, autoimmune polyneuritis, multiple sclerosis, experimental allergic encephalomyelitis, pemphigus and other bullous diseases, rheumatic carditis, Goodpasture's syndrome, postcardiotomy syndrome, systemic lupus erythematosus, rheumatoid arthritis, Sjorgen's syndrome, polymyositis, dermatomyositis, scleroderma, Chron's disease, ulcerative colitis, chronic obstructive pulmonary diseases; chronic inflammatory diseases; allergic diseases: asthma, atopic dermatitis; and fibrotic diseases.

30. The method according to any of claim 13, 21 or 28 wherein the CD4$^+$ T cells comprise CD4$^+$CD25$^+$ Tr cells.

31. The method according to claim 30 wherein the CD4$^+$ T cells also comprise CD4$^+$CD25$^-$ T cells.

* * * * *